United States Patent
Kuo et al.

(10) Patent No.: US 7,425,649 B2
(45) Date of Patent: Sep. 16, 2008

(54) 4-((PHENOXYALKYL)THIO)-PHENOXYACETIC ACIDS AND ANALOGS

(75) Inventors: Gee-Hong Kuo, Scotch Plains, NJ (US); Rui Zhang, Belle Mead, NJ (US); Aihua Wang, Jamison, PA (US); Alan DeAngelis, Pennington, NJ (US); Keith Demarest, Flemington, NJ (US); Patricia Pelton, Long Valley, NJ (US)

(73) Assignee: Janssen Pharmaceutica N.V. (BE)

( * ) Notice: Subject to any disclaimer, the term of this patent is extended or adjusted under 35 U.S.C. 154(b) by 205 days.

(21) Appl. No.: 11/226,645

(22) Filed: Sep. 14, 2005

(65) Prior Publication Data

US 2006/0058382 A1    Mar. 16, 2006

Related U.S. Application Data

(60) Provisional application No. 60/609,967, filed on Sep. 15, 2004.

(51) Int. Cl.
- C07C 59/00 (2006.01)
- C07C 53/134 (2006.01)
- C07C 255/00 (2006.01)
- A61K 31/275 (2006.01)
- A61K 31/20 (2006.01)
- A61K 31/195 (2006.01)

(52) U.S. Cl. .................. 562/470; 562/496; 514/521; 514/559; 514/561; 514/599; 558/410

(58) Field of Classification Search .................. None
See application file for complete search history.

(56) References Cited

U.S. PATENT DOCUMENTS

| 4,125,732 A | 11/1978 | McEvoy et al. |
| 2003/0225158 A1* | 12/2003 | Auerbach et al. ............ 514/456 |

FOREIGN PATENT DOCUMENTS

| JP | 10195057 A | 7/1998 |
| WO | WO 9728115 A | 8/1997 |
| WO | WO 02/062774 A | 8/2002 |
| WO | WO 02/100813 A | 12/2002 |

OTHER PUBLICATIONS

Oliver, B. et al., "Differential Expression of Peroxisome Proliferator-Activated Receptors (PPARs): Tissue Distribution of PPAR-α, -β, and -γ in the Adult Rat." *Endocrinology*, 1996, 354-366, 137, No. 1.
Boden, G. "Free Fatty Acids, Insulin Resistance, and Type 2 Diabetes Mellitus." *PAAP*, 1999, 241-248, vol. 111, No. 3.
Leibowitz, M. D. et al., "Activation of PPARδ alters lipid metabolism in db/db mice." *FEBS*, 2000, 333-336, vol. 473.
PCT International Search Report, dated Jun. 3, 2006 for PCT Appln. No. PCT/US2005/032938 which relates to U.S. Appl. No. 11/226,645, filed Sep. 14, 2005.
Written Opinion on the International Searching Authority for PCT Application No. PCT/US/2005/032938.

* cited by examiner

*Primary Examiner*—Sikarl A Witherspoon

(57) ABSTRACT

The invention features 4-((phenoxyalkyl)thio)-phenoxyacetic acids and analogs, compositions containing them, and methods of using them as PPAR modulators to treat or inhibit the progression of, for example, dyslipidemia.

40 Claims, No Drawings

4-((PHENOXYALKYL)THIO)-PHENOXYACETIC ACIDS AND ANALOGS

CROSS-REFERENCE TO RELATED APPLICATIONS

This Application claims priority to U.S. Provisional Patent Application No. 60/609,967, filed Sep. 15, 2004, which is hereby incorporated by reference in its entirety.

FIELD OF THE INVENTION

The invention features 4-((phenoxyalkyl)thio)-phenoxyacetic acids and analogs, compositions containing them, and methods of using them.

BACKGROUND

The peroxisome proliferator-activated receptors (PPARs) are metabolic sensors regulating the expression of genes involved in glucose and lipid homeostasis. Agonists of the PPARα subtype, such as LOPID® (gemfibrozil) and TRICOR® (fenofibrate), and agonists of the PPARγ subtype, such as AVANDIA® (rosiglitazone maleate), are used for the treatment of dyslipidemia and diabetes, respectively. Another member of this nuclear receptor family, the peroxisome proliferator-activated receptor delta (PPAR delta or PPARδ) is also a necessary transcription factor reported to be involved in regulating genes involved in lipid metabolism and energy expenditure. PPAR delta has been shown to act as a "gateway" receptor modulating the expression of the other PPARs (Shi et al., 2002, Proc Natl. Acad. Sci USA, 99(5): 2613-2618). Each receptor subtype has a distinct tissue distribution: 1) PPARα shows the highest expression in liver, 2) PPARγ appears primarily in adipose tissue, and 3) PPARδ has the widest distribution—ubiquitously in adult rat (Braissant et al., 1996, Endocrinology 137(1): 354-366) and in all the human tissues tested to date, including liver, kidney, abdominal adipose and skeletal muscle (Auboeuf et al., 1997, Diabetes 46(8):1319-1327).

The peroxisome proliferator-activated receptor alpha (PPAR alpha or PPARα) is a necessary transcription factor regulating genes relating to fatty acid metabolism and insulin action. The genes regulated by PPAR alpha include enzymes involved in the beta-oxidation of fatty acids, the liver fatty acid transport protein, and apo A1, an important component of high density lipoproteins (HDL). Selective, high affinity PPAR alpha agonists increase hepatic fatty acid oxidation, which in turn decreases circulating triglycerides and free fatty acids.

Examples of known PPAR alpha agonists variously useful for hyperlipidemia, diabetes, or atherosclerosis include fibrates such as fenofibrate (Fournier), gemfibrozil (Parke-Davis/Pfizer, Mylan, Watson), clofibrate (Wyeth-Ayerst, Novopharm), bezafibrate, and ciprofibrate and ureidofibrates such as GW 7647, GW 9578, and GW 9820 (GlaxoSmithKline).

Diabetes is a disease caused, or contributed to, by multiple factors and characterized by hyperglycemia which may be associated with increased and premature mortality due to an increased risk for microvascular and macrovascular diseases such as nephropathy, neuropathy, retinopathy, atherosclerosis, polycystic ovary syndrome (PCOS), hypertension, ischemia, stroke, and heart disease. Type I diabetes (IDDM) results from genetic deficiency of insulin, the hormone regulating glucose metabolism. Type II diabetes is known as non-insulin dependent diabetes mellitus (NIDDM), and is due to a profound resistance to insulin regulatory effect on glucose and lipid metabolism in the main insulin-sensitive tissues, i.e., muscle, liver and adipose tissue. This insulin resistance or reduced insulin sensitivity results in insufficient insulin activation of glucose uptake, oxidation and storage in muscle and inadequate insulin repression of lipolysis in adipose tissue as well as glucose production and secretion in liver. Many Type II diabetics are also obese, and obesity is believed to cause and/or exacerbate many health and social problems such as coronary heart disease, stroke, obstructive sleep apnoea, gout, hyperlipidemia, osteoarthritis, reduced fertility, and impaired psychosocial function.

A class of compounds, thiazolidinediones (glitazones), have been suggested to be capable of ameliorating many symptoms of NIDDM by binding to the peroxisome proliferator activated receptor (PPAR) family of receptors. They increase insulin sensitivity in muscle, liver and adipose tissue in several animal models of NIDDM resulting in correction of the elevated plasma levels of glucose, triglycerides and non-esterified free fatty acids without any occurrence of hypoglycemia. However, undesirable effects have occurred in animal and/or human studies including cardiac hypertrophy, hemadilution and liver toxicity.

Many PPARγ agonists currently in development have a thiazolidinedione ring as a common structural element. PPARγ agonists have been demonstrated to be extremely useful for the treatment of NIDDM and other disorders involving insulin resistance. Troglitazone, rosiglitazone, and pioglitazone have been approved for treatment of Type II diabetes in the United States. There is also some indication that benzimidazole-containing thiazolidinedione derivatives may be used to treat irritable bowel disorder (IBD), inflammation, and cataracts (JP 10195057).

Cardiovascular disease (CVD) is prevalent in the world and is often associated with other disease states such as diabetes and obesity. Many population studies have attempted to identify the risk factors for CVD; of these, high plasma levels of low density lipoprotein cholesterol (LDL-C), high plasma levels of triglycerides (>200 mg/dl), and low levels of high density lipoprotein cholesterol (HDL-C) are considered to be among the most important. Currently, there are few therapies targeting low HDL-C and triglycerides.

Recently, potent ligands for PPARδ have been published, providing a better understanding of its function in lipid metabolism. The main effect of these compounds in db/db mice (Leibowitz et al., 2000, FEBS Lett. 473(3):333-336) and obese rhesus monkeys (Oliver et al., 2001, Proc. Natl. Acad. Sci. USA 98(9):5306-5311) was an increase in high density lipoprotein cholesterol (HDL-C) and a decrease in triglycerides, with little effect on glucose (although insulin levels were decreased in monkeys). HDL-C removes cholesterol from peripheral cells through a process called reverse cholesterol transport. The first and rate-limiting step, a transfer of cellular cholesterol and phospholipids to the apolipoprotein A-I component of HDL, is mediated by the ATP binding cassette transporter A1 (ABCA1) (Lawn et al., 1999, J. Clin. Investigation 104(8): R25-R31). PPARδ activation has been shown to increase HDL-C level through transcriptional regulation of ABCA1 (Oliver et al., 2001, Proc. Natl. Acad. Sci. USA 98(9): 5306-5311). Through induction of ABCA1 mRNA expression in macrophages, PPARδ agonists may increase HDL-C levels in patients and remove excess cholesterol from lipid-laden macrophages, thereby inhibiting the development of atherosclerotic lesions. Existing therapy for hypercholesterolemia includes the statin drugs, which decrease LDL-C but show little effect on HDL-C, and the fibrates, the PPARα agonists that have low potency and induce only modest HDL-C elevation. In addition, like the fibrates, PPARδ agonists may also reduce triglycerides, an additional risk factor for cardiovascular disease and diabetes. Elevated free fatty acid level has been shown to contribute to insulin resistance and progression of diabetes (Boden, G. PROCEEDINGS OF THE ASSOCIATION OF AMERICAN PHYSICIANS (1999 May-June), 111(3), 241-8).

Examples of known PPAR delta agonists variously useful for hyperlipidemia, diabetes, or atherosclerosis include L-165041 (Leibowitz et al., 2000) and GW501516 (Oliver et al., Proceedings of the National Academy of Sciences of the United States of America (2001), 98(9), 5306-5311). Treatment of differentiated THP-1 monocytes with GW501516 induced ABCA1 mRNA expression and enhanced cholesterol efflux from these cells.

SUMMARY OF THE INVENTION

The invention features compounds of Formula (I) below:

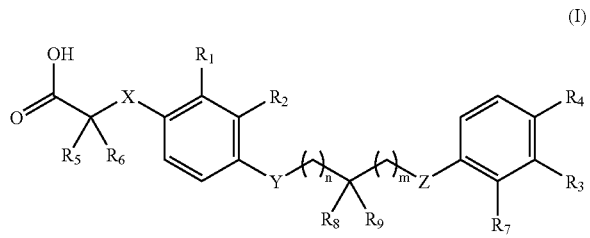

(I)

wherein

X is selected from a covalent bond, S, and O;

Y is S or O;

Z is O or $CH_2$, provided when Y is O, then Z is O;

$R_1$ and $R_2$ are independently selected from H, $C_{1-3}$ alkyl, $C_{1-3}$ alkoxy, halo, and $NR_aR_b$ wherein $R_a$ and $R_b$ are independently H or $C_{1-3}$ alkyl;

$R_3$ and $R_4$ are independently selected from H, halo, cyano, $C_{1-5}$ alkyl, hydroxy, $C_{2-4}$ acyl, $C_{1-4}$ alkoxy, and $NR_cR_d$ wherein $R_c$ and $R_d$ are independently H or $C_{1-3}$ alkyl, provided that $R_3$ and $R_4$ are not both H;

$R_5$ and $R_6$ are independently selected from H, $C_{1-8}$ alkyl and substituted $C_{1-8}$ alkyl, provided that $R_5$ and $R_6$ are not both H;

$R_7$ is selected from H, halo, $C_{1-8}$ alkyl, and phenyl;

$R_8$ and $R_9$ are independently selected from halo, phenyl, $C_{1-9}$ alkyl, $C_{1-8}$ alkoxy, $C_{2-9}$ alkenyl, $C_{2-9}$ alkenyloxy, $C_{3-7}$ cycloalkyl, $C_{3-7}$ cycloalkoxy, $C_{3-7}$ cycloalkyl-$C_{1-7}$ alkyl, $C_{3-7}$ cycloalkyl-$C_{1-7}$ alkoxy, $C_{3-7}$ cycloalkyloxy-$C_{1-6}$ alkyl, and $C_{3-7}$ cycloalkyloxy-$C_{1-7}$ alkoxy, or $R_8$ and $R_9$ together form $C_{1-9}$ alkylidenyl or $C_{3-9}$ alkenylidenyl; or $R_8$, $R_9$ and the carbon atom to which they are attached together form $C_{3-7}$ cycloalkyl or 5- or 6-membered heterocyclyl;

n is 0, 1 or 2; and m is 0, 1 or 2;

or a pharmaceutically acceptable salt thereof.

The invention also features compositions that include one or more compounds of Formula (I) and a pharmaceutical carrier or excipient.

These compositions and the methods below may further include additional pharmaceutically active agents, such as lipid-lowering agents or blood-pressure lowering agents, or both.

Another aspect of the invention includes methods of using the disclosed compounds or compositions in various methods for treating, preventing, or inhibiting the progression of, a condition directly or indirectly mediated by PPAR delta. Said condition includes, but is not limited to, diabetes, nephropathy, neuropathy, retinopathy, polycystic ovary syndrome, hypertension, ischemia, stroke, irritable bowel disorder, inflammation, cataract, cardiovascular diseases, Metabolic X Syndrome, hyper-LDL-cholesterolemia, dyslipidemia (including hypertriglyceridemia, hypercholesterolemia, mixed hyperlipidemia, and hypo-HDL-cholesterolemia), atherosclerosis, obesity, and other disorders related to lipid metabolism and energy homeostasis complications thereof.

One embodiment of the present invention is a method for treating a PPAR mediated condition, such as a PPAR delta-mediated condition and optionally one or more PPAR alpha- or PPAR gamma-mediated conditions, which PPAR alpha-or PPAR gamma-mediated condition(s) may be the same as or different from said PPAR delta-mediated condition, said method comprising administering to a patient in need of treatment a pharmaceutically effective amount of a compound or composition described herein.

Another embodiment of the present invention is a method for inhibiting the onset and/or inhibiting the progression of a PPAR delta-mediated condition, said method comprising administering to a patient in need of treatment a pharmaceutically effective amount of a compound or composition described herein.

Examples of conditions that can be treated with a PPAR-delta agonist include, without limitation, diabetes, cardiovascular diseases, Metabolic X Syndrome, hypercholesterolemia, hypo-HDL-cholesterolemia, hyper-LDL-cholesterolemia, dyslipidemia, atherosclerosis, and obesity. Dyslipidemia includes hypertriglyceridemia, and mixed hyperlipidemia. For example, dyslipidemia (including hyperlipidemia) may be one or more of the following conditions: low HDL (<35 or 40 mg/dl), high triglycerides (>200 mg/dl), and high LDL (>150 mg/dl).

Examples of conditions that can be treated with a PPAR alpha-agonist include Syndrome X (or Metabolic Syndrome), dyslipidemia, high blood pressure, obesity, impaired fasting glucose, insulin resistance, Type II diabetes, atherosclerosis, hypercholesterolemia, hypertriglyceridemia, and non-alcoholic steatohepatitis.

Additional features and advantages of the invention will become apparent from the detailed discussion, examples, and claims below.

DETAILED DESCRIPTION

The invention features compositions containing compounds of Formula (I) in the above Summary section, and methods of using them.

Preferred compounds of the invention are PPAR delta agonists that have at least one and preferably two or three of the following characteristics when administered to patients with hypercholesterolemia, hypertriglyceridemia, low-HDL-C, obesity, diabetes and/or Metabolic X Syndrome: 1) increasing HDL-C level, 2) lowering triglycerides, 3) lowering free fatty acids, and 4) decreasing insulin levels. Improvement in HDL-C and triglyceride levels is beneficial for cardiovascular health. In addition, decreased level of triglycerides and free fatty acids contributes to reduce obesity and ameliorate or prevent diabetes.

According to one aspect of the invention, the compounds of the invention are dual PPAR compounds; in other words, they are both PPAR delta agonists and PPAR alpha agonists, preferably where the compound's $EC_{50}$ potency relating to PPAR delta is less than 0.2 µM and the potency relating to PPAR alpha is less than 3 µM. For example, more preferred dual PPAR alpha-delta agonists are those compounds having an $EC_{50}$ potency relating to PPAR delta that is less than 0.03 µM and where the potency relating to PPAR alpha is less than 1 µM.

According to another aspect of the invention, the compounds of the invention are pan-PPAR agonists, namely, compounds having PPAR alpha, PPAR delta, and PPAR gamma agonist activity, preferably where the $EC_{50}$ potency for PPAR delta is less than 0.2 µM; the potency for PPAR alpha is less than 3 µM; and the potency for PPAR gamma is less than 1 µM. More preferred pan-PPAR agonists have an $EC_{50}$ potency for PPAR delta that is less than 0.03 µM; a potency for PPAR alpha that is less than 1 µM; and a potency for PPAR gamma that is less than 0.7 µM.

PPAR delta, being ubiquitously expressed, can act as a gateway receptor that regulates the expression/activity of other nuclear receptors such as other PPARs. For instance, PPAR delta has been shown to block PPARγ-mediated adipogenesis and acyl-CoA oxidase expression; it has also been shown to be associated with the nuclear receptor corepressors SMRT (silencing mediator for retinoid and thyroid hormone receptors), SHARP (SMART and histone deacetylase-associated repressor protein), and HDACs (histone deacetylase). Thus, conditions directly mediated by these nuclear receptors, such as obesity and Type II diabetes, can be indirectly mediated by PPAR delta (See, for example, Shi et al., 2002, Proc Natl. Acad. Sci USA, 99(5): 2613-2618).

Some aspects of the invention relate to treating hypertriglyceridemia, raising levels of HDL, lowering levels of LDL, and/or lowering total cholesterol. Preferably, the methods of treatment are associated with improvements in the extent, duration, or degree of side effects, such as edema, normally associated with other existing therapies.

The invention is further described below. The specification is arranged as follows: A) Terms; B) Compounds; C) Synthesis; D) Formulation and Administration; E) Use; F) Biological Examples; G) Other Embodiments; and claims.

A. Terms

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation, prevention, treatment, or the delay of the onset or progression of the symptoms of the disease or disorder being treated.

Conditions directly or indirectly mediated by PPAR delta include, but are not limited to, diabetes, cardiovascular diseases, Metabolic X Syndrome, hypercholesterolemia, hypo-HDL-cholesterolemia, hyper-LDL-cholesterolemia, dyslipidemia, atherosclerosis, and obesity.

For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

Unless otherwise noted, as used herein and whether used alone or as part of a substituent group, "alkyl" and "alkoxy" include straight and branched chains having 1 to 8 carbon atoms, such as $C_{1-6}$, $C_{1-4}$, $C_{3-8}$, $C_{2-5}$, or any other range, and unless otherwise noted, include both substituted and unsubstituted moieties. For example, $C_{1-6}$ alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are formed from the previously described straight or branched chain alkyl groups. "Alkyl" and "alkoxy" include unsubstituted or substituted moieties with one or more substitutions, such as between 1 and 5, 1 and 3, or 2 and 4 substituents. The substituents may be the same (dihydroxy, dimethyl), similar (chloro, fluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, trifluoromethyl, and 3-iodocyclopentyl), hydroxyalkyl (such as hydroxymethyl, hydroxyethyl, 2-hydroxypropyl), aminoalkyl (such as aminomethyl, 2-aminoethyl, 3-aminopropyl, and 2-aminopropyl), alkoxylalkyl, nitroalkyl, alkylalkyl, cyanoalkyl, phenylalkyl, heteroarylalkyl, heterocyclylalkyl, phenoxyalkyl, heteroaryloxyalkyl (such as 2-pyridyloxyalkyl), heterocyclyloxy-alkyl (such as 2-tetrahydropyranoxyalkyl), thioalkylalkyl (such as MeS-alkyl), thiophenylalkyl (such as phS-alkyl), carboxylalkyl, and so on. A di($C_{1-3}$ alkyl) amino group includes independently selected alkyl groups, to form, for example, methylpropylamino and isopropylmethylamino, in addition dialkylamino groups having two of the same alkyl group such as dimethyl amino or diethylamino.

The term "alkenyl" includes optionally substituted straight chain and branched hydrocarbon radicals as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl includes cycloalkenyl. Cis and trans or (E) and (Z) forms are included within the invention. "Alkenyl" may be substituted with one or more substitutions including, but not limited to, cyanoalkenyl, and thioalkenyl.

The term "alkynyl" includes optionally substituted straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

The term "Ac" as used herein, whether used alone or as part of a substituent group, means acetyl ($CH_3CO—$). The term "acyl" as used herein, referes to a substituent that has a carbonyl group ($C=O$) and one or more alkyl or alkylene groups. For example, $C_{2-4}$ acyl includes without limitation, acetyl, $CH_3CH_2—(C=O)—CH_2—$, and $CH_3\ CH_2\ CH_2\ (C=O)—$.

The term "halogen" or "halo" shall include iodo, bromo, chloro and fluoro.

The terms "aryl" or "Ar" as used herein refer to an unsubstituted or substituted aromatic hydrocarbon ring system such as phenyl and naphthyl. When the Ar or aryl group is substituted, it may have one to three substituents which are independently selected from $C_1$-$C_8$ alkyl, $C_1$-$C_8$ alkoxy, fluorinated $C_1$-$C_8$ alkyl (e.g., trifluoromethyl), fluorinated $C_1$-$C_8$ alkoxy (e.g., trifluoromethoxy), halogen, cyano, $C_1$-$C_8$ alkylcarbonyl such as acetyl, carboxyl, hydroxy, amino, nitro, $C_1$-$C_4$ alkylamino (i.e., $—NH—C_1$-$C_4$ alkyl), $C_1$-$C_4$ dialkylamino (i.e., $—N—[C_1$-$C_4$ alkyl$]_2$ wherein the alkyl groups can be the same or different), or unsubstituted, mono-, di- or tri-substituted phenyl wherein the substituents on the phenyl are independently selected from $C_1$-$C_8$ alkyl, $C_1$-$C_8$ alkoxy, fluorinated $C_1$-$C_8$ alkyl, fluorinated $C_1$-$C_8$ alkoxy, halogen, cyano, acetyl, carboxyl, hydroxy, amino, nitro, alkylamino, dialkylamino or five or six membered heteroaryl having 1-3 heteroatoms selected from N, O and S.

The term "heteroaryl" as used herein represents a stable, unsubsituted or substituted five or six membered monocyclic or bicyclic aromatic ring system which consists of carbon atoms and from one to three heteroatoms selected from N, O and S. The heteroaryl group may be attached at any heteroatom or carbon atom which results in the creation of a stable structure. Examples of heteroaryl groups include, but are not limited to, benzimidazolyl, benzisoxazolyl, benzofuranyl, benzopyrazolyl, benzothiadiazolyl, benzothiazolyl, benzothienyl, benzotriazolyl , benzoxazolyl, furanyl, furazanyl, furyl, imidazolyl, indazolyl, indolizinyl, indolinyl, indolyl, isobenzofuranyl, isoindolyl, isothiazolyl, isoxazolyl, oxazolyl, purinyl, pyrazinyl, pyrazolyl, pyridazinyl, pyridinyl, pyrimidinyl, pyrrolyl, quinolinyl, quinolyl, thiadiazolyl, thiazolyl, thiophenyl, or triazolyl. When the heteroaryl group is substituted, the heteroaryl group may have one to three substituents including, but not limited to, $C_1$-$C_8$ alkyl, halogen, and aryl.

The term "heterocyclyl" includes optionally substituted nonaromatic rings having carbon atoms and at least one heteroatom (O, S, N) or heteroatom moiety ($SO_2$, CO, CONH, COO) in the ring. A heterocyclyl may be saturated, partially saturated, nonaromatic, or fused. Examples of heterocyclyl include cyclohexylimino, imdazolidinyl, imidazolinyl, morpholinyl, piperazinyl, piperidyl, pyridyl, pyranyl, pyrazolidinyl, pyrazolinyl, pyrrolidinyl, pyrrolinyl, and thienyl.

Unless otherwise indicated, heteroaryl and heterocyclyl may have a valence connecting it to the rest of the molecule through a carbon atom, such as 3-furyl or 2-imidazolyl, or through a heteroatom, such as N-piperidyl or 1-pyrazolyl. Preferably a monocyclic heterocyclyl has between 5 and 7 ring atoms, or between 5 and 6 ring atoms; there may be between 1 and 5 heteroatoms or heteroatom moieties in the ring, and preferably between 1 and 3, or between 1 and 2 heteroatoms or heteroatom moieties.

Heterocyclyl and heteroaryl also include fused, e.g., bicyclic, rings, such as those optionally fused with an optionally substituted carbocyclic or heterocyclic five- or six-membered aromatic ring. For example, "heteroaryl" includes an optionally substituted six-membered heteroaromatic ring containing 1, 2 or 3 nitrogen atoms fused with an optionally substituted five- or six-membered carbocyclic or heterocyclic aromatic ring. Said heterocyclic five-or six-membered aromatic ring fused with the said five- or six-membered aromatic ring may contain 1, 2 or 3 nitrogen atoms where it is a six-membered ring, or 1, 2 or 3 heteroatoms selected from oxygen, nitrogen and sulfur where it is a five-membered ring.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Where chemical moieties are combined, such as in ethoxymethyl or phenylethyl, the term is described in the direction from the periphery to the connection point of the rest of the molecule. For example, ethoxymethyl is $CH_3CH_2OCH_2—$ and phenylethyl is a phenyl group linked by $—CH_2CH_2—$ to the rest of the molecule (and not a phenyl group linked to the molecule with a $CH_3CH_2$ group as a substituent on the phenyl.) Where parentheses are used, they indicate a peripheral substitution.

As used herein, the term "composition" is intended to encompass a product comprising the specified ingredients in the specified amounts, as well as any product which results, directly or indirectly, from combinations of the specified ingredients in the specified amounts.

Compounds of the invention are further described in the next section.

B. Compounds

The present invention features compositions containing and methods of using compounds of Formula (I) as described above. Unless otherwise noted, in Formula (I), each hydrocarbyl (alkyl, alkenyl, alkynyl, cycloalkyl, cycloalkenyl, etc) or heterocarbyl (heterocyclyl, heteroaryl, heteroatom moiety such as sulfonyl, amino, amido, etc.) may be substituted or unsubstituted, for example, "alkyl" includes substituted and unsubstituted alkyl and "heterocyclyl" and "aryl" and "alkoxy" and so on, may also be substituted or unsubstituted. For example, where $R_4$ is "methyl or methoxy", unless otherwise indicated, these terms collectively include: methyl, methoxy, trifluoromethyl, trifluoromethoxy, difluoromethyl, difluoromethoxy, fluoromethyl, fluoromethoxy, chlorodifluoromethyl, chlorodifluoromethoxy, dichlorofluoromethyl, and dichlorofluoromethoxy, and so on.

Examples include those compounds wherein: (a) X is S or O; (b) X is a covalent bond; (c) X is O; (d) Y is O; (e) Y is S; (f) Z is O; (g) Z is CH or $CH_2$; (h) m is 1; (i) m is 2; (k) n is 1; (l) $R_1$ and $R_2$ are independently selected from H, $C_{1-3}$ alkyl, $C_{1-3}$ alkoxy, F, Cl, and Br; (m) $R_1$ and $R_2$ are independently selected from H, methyl, methoxy, F and Cl; (n) $R_3$ and $R_4$ are independently selected from H, halo, cyano, acetyl, $C_{1-2}$ alkyl, and $C_{1-2}$ alkoxy; (o) $R_3$ is independently selected from H, F, Cl, methyl, and methoxy; (p) $R_4$ is independently selected from H, halo, cyano, $C_{1-2}$ alkyl, and $C_{1-2}$ alkoxy; (q) $R_3$ is independently selected from H, halo, cyano, $C_{1-2}$ alkyl, and $C_{1-2}$ alkoxy, and $R_4$ is independently selected from F, Cl, methyl, and methoxy; (r) $R_3$ is selected from methyl, methoxy, H, Cl, Br, I, OH, $—CH(CF_3)_2$, $CF_3$, $—OCF_3$, $—N$ (CH$_3$)$_2$, —O—CH$_2$COOH, and —COCH$_3$, and R$_4$ is selected from H, Cl, and methyl; (s) R$_8$ and R$_9$ together form C$_{1-9}$ alkylidenyl or C$_{3-9}$ alkenylidenyl, or R$_8$, R$_9$ and the carbon atom to which they attach together form C$_{3-7}$ cycloalkyl; (t) R$_8$ and R$_9$ are independently selected from halo, phenyl, C$_{1-9}$ alkyl, C$_{1-8}$ alkoxy, C$_{2-9}$ alkenyl, C$_{2-9}$ alkenyloxy, C$_{3-7}$ cycloalkyl, C$_{3-7}$ cycloalkoxy, C$_{3-7}$cycloalkyl-C$_{1-7}$alkyl, C$_{3-7}$cycloalkyl-C$_{1-7}$alkoxy, C$_{3-7}$cycloalkyloxy-C$_{1-6}$alkyl, and C$_{3-7}$cycloalkyloxy-C$_{1-7}$alkoxy; (u) R$_3$ is selected from H, F, Cl, methyl, and methoxy, and R$_4$ is selected from F, Cl, acetyl, methyl, methoxy, trifluoromethyl, trifluoromethoxy, difluoromethyl, difluoromethoxy, fluoromethyl, fluoromethoxy; (v) R$_1$ is selected from H, CF$_3$, methyl, Cl, and methoxy, and R$_2$ is selected from H, Cl, and methyl; (w) X is O, and Y is O; (x) Z is O and Y is O; (y) R$_1$ is selected from H, CF$_3$, methyl, Cl, and methoxy, R$_2$ is selected from H, Cl, and methyl, R$_3$ is selected from H, F, Cl, methyl, and methoxy, and R$_4$ is selected from F, Cl, methyl, and methoxy; (z) X is O, Y is O, R$_3$ is selected from H, F, Cl, methyl, and methoxy, and R$_4$ is selected from F, Cl, methyl, and methoxy; (z2) Z is O, Y is O, R$_3$ is selected from H, F, Cl, methyl, and methoxy, and R$_4$ is selected from F, Cl, methyl, and methoxy; (aa) R$_1$ is selected from H, CF$_3$, methyl, Cl, and methoxy, R$_2$ is selected from H, Cl, and methyl, R$_3$ is selected from H, F, Cl, methyl, and methoxy, R$_4$ is selected from F, Cl, methyl, and methoxy, and R$_5$ and R$_6$ together form C$_{1-9}$ alkylidenyl or C$_{3-9}$ alkenylidenyl, or R$_8$, R$_9$ and the carbon atom to which they attach together form C$_{3-7}$ cycloalkyl; (bb) X is O, Y is O, Z is O, R$_1$ is selected from H, CF$_3$, methyl, Cl, and methoxy, R$_2$ is selected from H, Cl, and methyl, R$_3$ is selected from H, F, Cl, methyl, and methoxy, R$_4$ is selected from F, Cl, methyl, and methoxy, and R$_8$ and R$_9$ are independently selected from halo, phenyl, C$_{1-9}$ alkyl, C$_{1-8}$ alkoxy, C$_{2-9}$ alkenyl, C$_{2-9}$ alkenyloxy, C$_{3-7}$ cycloalkyl, C$_{3-7}$ cycloalkoxy, C$_{3-7}$cycloalkyl-C$_{1-7}$alkyl, C$_{3-7}$cycloalkyl-C$_{1-7}$alkoxy, C$_{3-7}$cycloalkyloxy-C$_{1-6}$alkyl, and C$_{3-7}$cycloalkyloxy-C$_{1-7}$alkoxy; (cc) X is O, Y is O, Z is O, R$_1$ is selected from H, CF$_3$, methyl, Cl, and methoxy, R$_2$ is selected from H, Cl, and methyl, R$_3$ is selected from H, F, Cl, methyl, and methoxy, and R$_4$ is selected from F, Cl, methyl, and methoxy; (dd) X is O, Y is O, Z is O, R$_1$ is selected from H, CF$_3$, methyl, Cl, and methoxy, R$_2$ is selected from H, Cl, and methyl, R$_3$ is selected from H, F, Cl, methyl, and methoxy, R$_4$ is selected from F, Cl, methyl, and methoxy, and R$_8$ and R$_9$ together form C$_{1-9}$ alkylidenyl or C$_{3-9}$ alkenylidenyl, or R$_8$, R$_9$ and the carbon atom to which they attach together form C$_{3-7}$ cycloalkyl; (ee) X is O, Y is O, Z is O, R$_1$ is selected from H, CF$_3$, methyl, Cl, and methoxy, R$_2$ is selected from H, Cl, and methyl, R$_3$ is selected from H, F, Cl, methyl, and methoxy, R$_4$ is selected from F, Cl, methyl, and methoxy, and R$_8$ and R$_9$ are independently selected from halo, phenyl, C$_{1-9}$alkyl, C$_{1-8}$ alkoxy, C$_{2-9}$ alkenyl, C$_{2-9}$ alkenyloxy, C$_{3-7}$ cycloalkyl, C$_{3-7}$ cycloalkoxy, C$_{3-7}$cycloalkyl-C$_{1-7}$alkyl, C$_{3-7}$cycloalkyl-C$_{1-7}$alkoxy, C$_{3-7}$cycloalkyloxy-C$_{1-6}$alkyl, and C$_{3-7}$cycloalkyloxy-C$_{1-7}$alkoxy; (ff) X is O, Y is O or S, Z is O, R$_1$ is selected from H, CF$_3$, methyl, Cl, and methoxy, R$_2$ is selected from H, Cl, and methyl, R$_3$ is selected from H, F, Cl, methyl, and methoxy, R$_4$ is selected from F, Cl, methyl, and methoxy, m is 1, and n is 1; (gg) X is O, Y is O or S, Z is O, R$_1$ is selected from H, CF$_3$, methyl, Cl, and methoxy, R$_2$ is selected from H, Cl, and methyl, R$_3$ is selected from H, F, Cl, methyl, and methoxy, R$_4$ is selected from F, Cl, methyl, and methoxy, m is 1, n is 1, and R$_8$ and R$_9$ are independently selected from halo, phenyl, C$_{1-9}$ alkyl, C$_{1-8}$ alkoxy, C$_{2-9}$ alkenyl, C$_{2-9}$ alkenyloxy, C$_{3-7}$ cycloalkyl, C$_{3-7}$ cycloalkoxy, C$_{3-7}$cycloalkyl-C$_{1-7}$alkyl, C$_{3-7}$cycloalkyl-C$_{1-7}$alkoxy, C$_{3-7}$cycloalkyloxy-C$_{1-6}$alkyl, and C$_{3-7}$cycloalkyloxy-C$_{1-7}$alkoxy; (hh) R$_5$ and R$_6$ are C$_{1-4}$ alkyl; (ii) R$_5$ and R$_6$ are methyl; (jj) R$_5$ and R$_6$ are both methyl, both X and Z are O, R$_7$ is H, and R$_8$ and R$_9$ form =CH$_2$; or combinations of the above.

Compounds of the present invention further can be selected from:

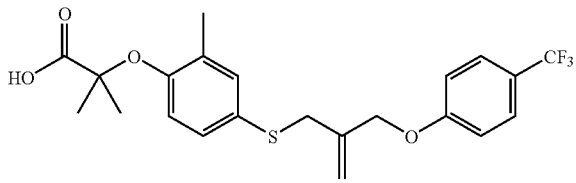

Compound 1

2-Methyl-2-{2-methyl-4-[2-(4-trifluoromethyl-phenoxymethyl)-allylsulfanyl]-phenoxy}-propionic Acid

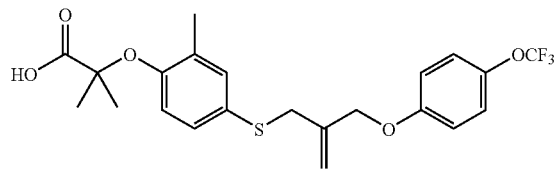

Compound 2

2-Methyl-2-{2-methyl-4-[2-(4-trifluoromethoxy-phenoxymethyl)-allylsulfanyl]-phenoxy}-propionic Acid

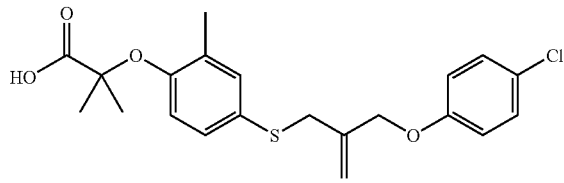

Compound 3

2-{4-[2-(4-Chloro-phenoxymethyl)-allylsulfanyl]-2-methyl-phenoxy}-2-methyl-propionic Acid

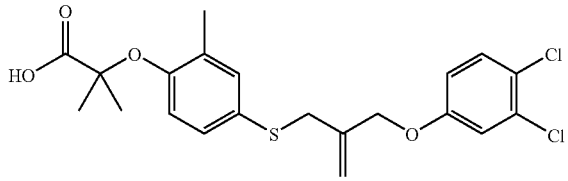

Compound 4

2-{4-[2-(3,4-Dichloro-phenoxymethyl)-allylsulfanyl]-2-methyl-phenoxy}-2-methyl-propionic Acid Compound 5

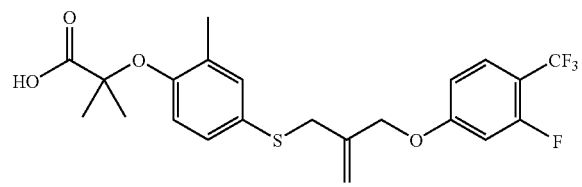

2-{4-[2-(3-Fluoro-4-trifluoromethyl-phenoxymethyl)-allylsulfanyl]-2-methyl-phenoxy}-2-methylpropionic Acid Compound 6

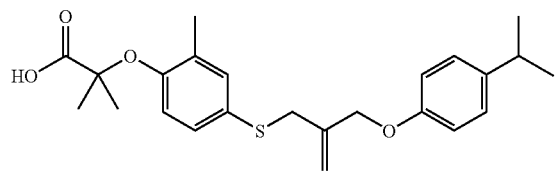

2-{4-[2-(4-Isopropyl-phenoxymethyl)-allylsulfanyl]-2-methyl-phenoxy}-2-methyl-propionic Acid Compound 7

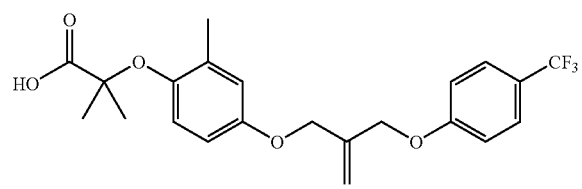

2-Methyl-2-{2-methyl-4-[2-(4-trifluoromethyl-phenoxymethyl)-allyloxy]-phenoxy}-propionic Acid Compound 8

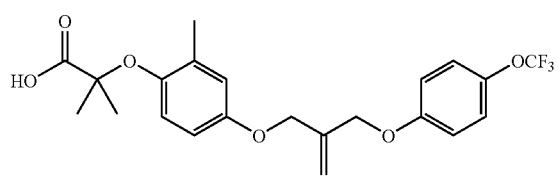

2-Methyl-2-{2-methyl-4-[2-(4-trifluoromethoxy-phenoxymethyl)-allyloxy]-phenoxy}-propionic Acid Compound 9

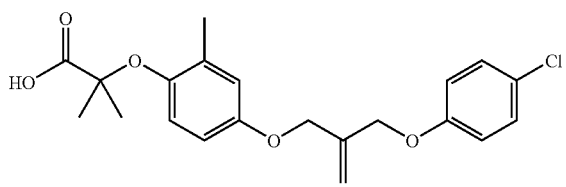

2-{4-[2-(4-Chloro-phenoxymethyl)-allyloxy]-2-methyl-phenoxy}-2-methyl-propionic Acid Compound 10

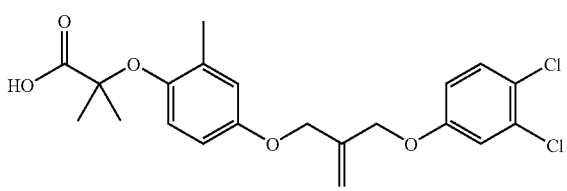

2-{4-[2-(3,4-Dichloro-phenoxymethyl)-allyloxy]-2-methyl-phenoxy}-2-methyl-propionic Acid Compound 11

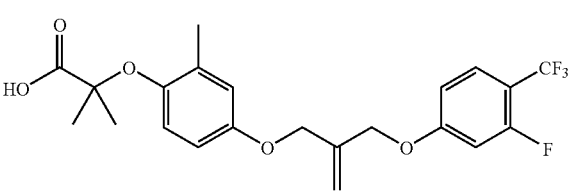

2-{4-[2-(3-Fluoro-4-trifluoromethyl-phenoxymethyl)-allyloxy]-2-methyl-phenoxy}-2-methyl-propionic Acid Compound 12

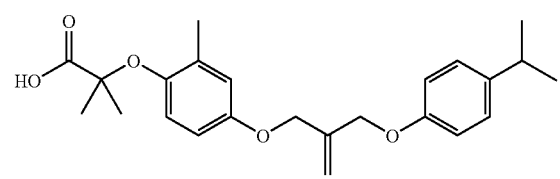

2-{4-[2-(4-Isopropyl-phenoxymethyl)-allyloxy]-2-methyl-phenoxy}-2-methyl-propionic Acid A preferred compound is listed in Table 1:

TABLE 1

| Compound Number | Structure |
|---|---|
| 1 | HO₂C—C(CH₃)₂—O—[2-methylphenyl]—S—CH₂—C(=CH₂)—CH₂—O—[phenyl]—CF₃ |

The pharmaceutical compounds of the invention include a pharmaceutical composition comprising a pharmaceutically acceptable carrier and a compound described above.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The invention provides the disclosed compounds and closely related, pharmaceutically acceptable forms of the disclosed compounds, such as salts, esters, amides, hydrates or solvated forms thereof; masked or protected forms; and racemic mixtures, or enantiomerically or optically pure forms.

Pharmaceutically acceptable salts, esters, and amides include carboxylate salts (e.g., $C_{1-8}$ alkyl, cycloalkyl, aryl, heteroaryl, or non-aromatic heterocyclic) amino acid addition salts, esters, and amides which are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S. M. Berge, et al., "Pharmaceutical Salts," J. Pharm. Sci., 1977, 66:1-19, which is incorporated herein by reference. Representative pharmaceutically acceptable amides of the invention include those derived from ammonia, primary $C_{1-6}$ alkyl amines and secondary di($C_{1-6}$ alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di($C_{1-2}$ alkyl)amines. Representative pharmaceutically acceptable esters of the invention include $C_{1-7}$ alkyl, $C_{5-7}$ cycloalkyl, phenyl, and phenyl($C_{1-6}$)alkyl esters. Preferred esters include methyl esters.

The invention also includes disclosed compounds having one or more functional groups (e.g., amino, or carboxyl) masked by a protecting group. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(Imidazol-1-ylmethyl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate(tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate Sulfonates Examples of sulfonates include sulfate, methanesulfonate (mesylate), benzylsulfonate, and tosylate.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of Amides Include

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitriphenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special—NH Protective Groups

Examples of special NH protective groups include

N-Alkyl and N-Aryl Amines

N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl)mesityl]methylene, and N-(N',N'-dimethylaminomethylene).

Protection for the Carboxyl Group

Esters

Examples of esters include form ate, benzoylformate, acetate, trichloroacetate, trifluoroacetate, methoxyacetate, phenoxyacetate, p-chlorophenoxyacetate, benzoate.

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

C. Synthesis

The invention provides methods of making the disclosed compounds according to traditional organic synthetic methods as well as matrix or combinatorial synthetic methods. Schemes A through G describe suggested synthetic routes. Using these Schemes, the guidelines below, and the examples, a person of skill in the art may develop analogous or similar methods for a given compound that are within the invention. These methods are representative of the preferred synthetic schemes, but are not to be construed as limiting the scope of the invention.

One skilled in the art will recognize that synthesis of the compounds of the present invention may be effected by purchasing an intermediate or protected intermediate compounds described in any of the schemes disclosed herein. One skilled in the art will further recognize that during any of the processes for preparation of the compounds in the present invention, it may be necessary and/or desirable to protect sensitive or reactive groups on any of the molecules concerned. This may be achieved by means of conventional protecting groups, such as those described in "Protective Groups in Organic Synthesis", John Wiley & Sons, 1991. These protecting groups may be removed at a convenient stage using methods known from the art.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation. The compounds may also be resolved by formation of diastereomeric esters or amides, followed by chromatographic separation and removal of the chiral auxiliary. Alternatively, the compounds may be resolved using a chiral HPLC column.

Examples using the preferred synthetic routes include Examples I and II. Compounds analogous to the target compounds of these examples can be made according to similar routes. The disclosed compounds are useful in basic research and as pharmaceutical agents as described in the next section.

General Guidance

A preferred synthesis of Formula (I) is demonstrated in Schemes A through G.

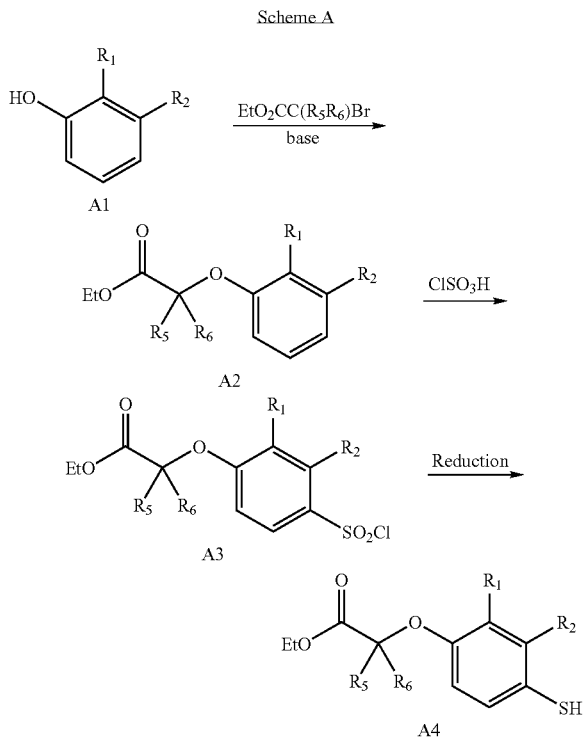

In accordance with Scheme A, wherein $R_1$, $R_2$, $R_5$ and $R_6$ are as described above (except that $R_5$ and $R_6$ do not form spiro $C_{3-6}$ cycloalkyl or spiro 5- or 6-membered heterocyclyl), phenol A1, a variety of which are commercially available (such as 3-methylphenol, 2-ethylphenol, 2-propylphenol, 2,3-dimethylphenol, 2-chlorophenol, 2,3-dichlorophenol, 2-bromophenol, and 2-aminophenol), is alkylated to form phenoxyacetic acid ethyl ester A2 with a suitable haloacetic acid ester such as bromoacetic acid ethyl ester or 2-bromo-2-methylpropionic acid ethyl ester, in the presence of an appropriate base such as $Cs_2CO_3$, $K_2CO_3$, or NaH, in a suitable solvent such as $CH_3CN$ or THF. Sulfonation of the phenoxyacetic acid ethyl ester A2 with an appropriate sulfonating agent, such as chlorosulfonic acid, occurs selectively at the para position to provide 4-chlorosulfonylphenoxyacetic acid ethyl ester A3. Transformation of the sulfonylchloride A3 to benzenethiol A4 is accomplished using a metal as a reducing agent, such as tin or zinc, in an acidic medium such as ethanol or dioxane.

In Schemes B, D, and E, $R_8$ and $R_9$ can be selected from, for example, H, $C_{1-8}$ alkyl, $C_{2-8}$ alkenyl, phenyl, halo, and cyano.

Scheme B

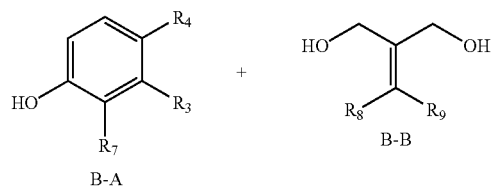

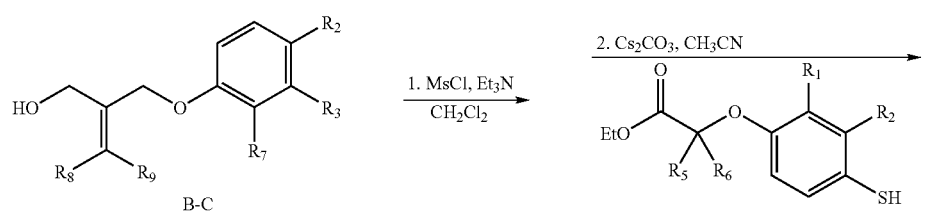

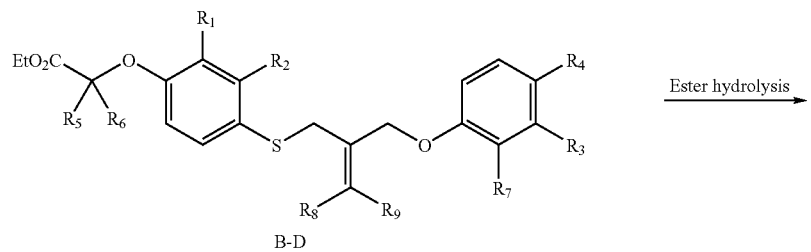

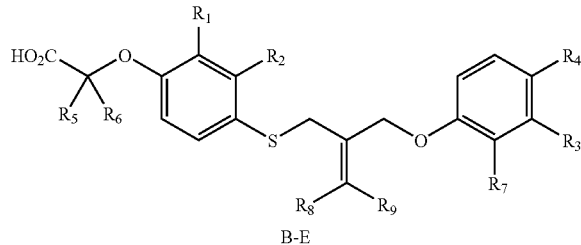

In Scheme B, Mitsunobu reaction of 1,3-diol B-B with phenol B-A provides alcohol B-C by employing a triarylphosphine such as triphenylphosphine, and an azodicarbonyl reagent such as diisopropyl azodicarboxylate, in a suitable solvent such as THF. Phenoxyacetic acid ethyl ester B-D is obtained in two steps: (1) conversion of the alcohol B-C to mesylate under standard conditions by employing methanesulfonyl chloride and triethylamine in an appropriate solvent such as $CH_2Cl_2$, and (2) alkylation of benzenethiol B-D, prepared according to Scheme A above, with the mesylate intermediate using a suitable base such as $Cs_2CO_3$, $K_2CO_3$, or NaH, in an appropriate solvent such as $CH_3CN$ or THF, under nitrogen. Under standard saponification conditions phenoxyacetic acid ethyl ester B-D is converted to acid B-E under nitrogen. The preferred hydrolysis conditions include using NaOH as a base in an aqueous alcoholic solvent system such as water-methanol, or using LiOH as a base in a milder water-THF system.

Scheme C

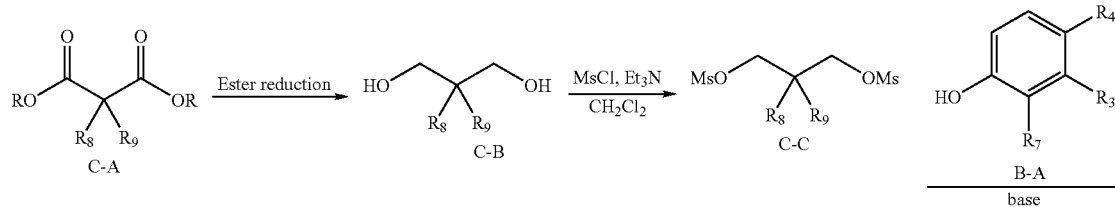

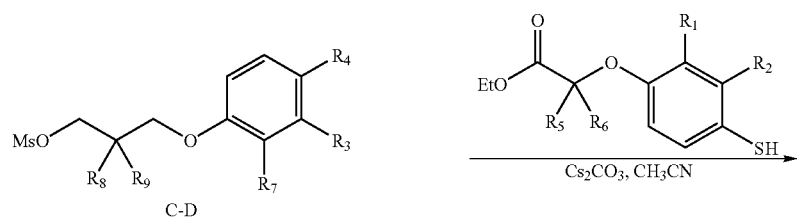

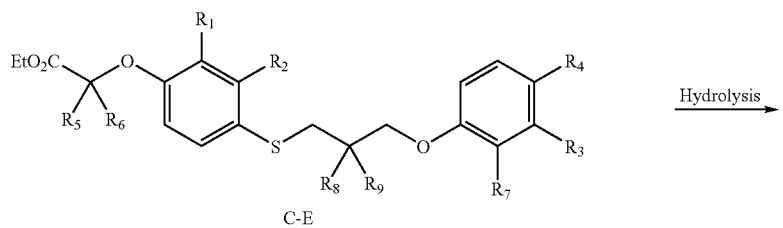

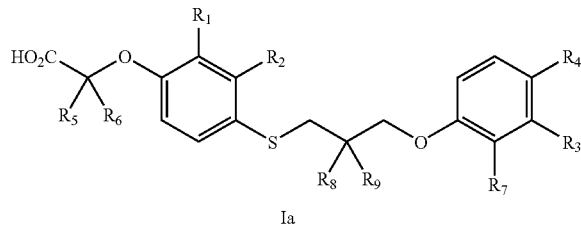

In Scheme C, $R_8$ and $R_9$ substituted malonate C-A is reduced to propane-1,3-diol C-B by using a suitable reducing agent such as lithium aluminum hydride or diisobutylaluminum hydride. After propane-1,3-diol C-B is converted to dimesylate C-C by using methanesulfonyl chloride and triethylamine in an appropriate solvent such as $CH_2Cl_2$, C-C reacts with phenol B-A in the presence of a suitable base such as $Cs_2CO_3$, $K_2CO_3$, or NaH in an appropriate solvent such as $CH_3CN$ or THF to produce mesylate C-D. Phenoxyacetic acid ethyl ester C-E is obtained by alkylation of benzenethiol A-D, prepared according to Scheme A above, with the mesylate C-D using a suitable base such as $Cs_2CO_3$, $K_2CO_3$, or NaH in an appropriate solvent such as $CH_3CN$ or THF under nitrogen. Under standard saponification conditions phenoxyacetic acid ethyl ester C-E is converted to acid Ia under nitrogen. The preferred hydrolysis conditions include using NaOH as a base in an aqueous alcoholic solvent system such as water-methanol, or using LiOH as a base in a milder water-THF system.

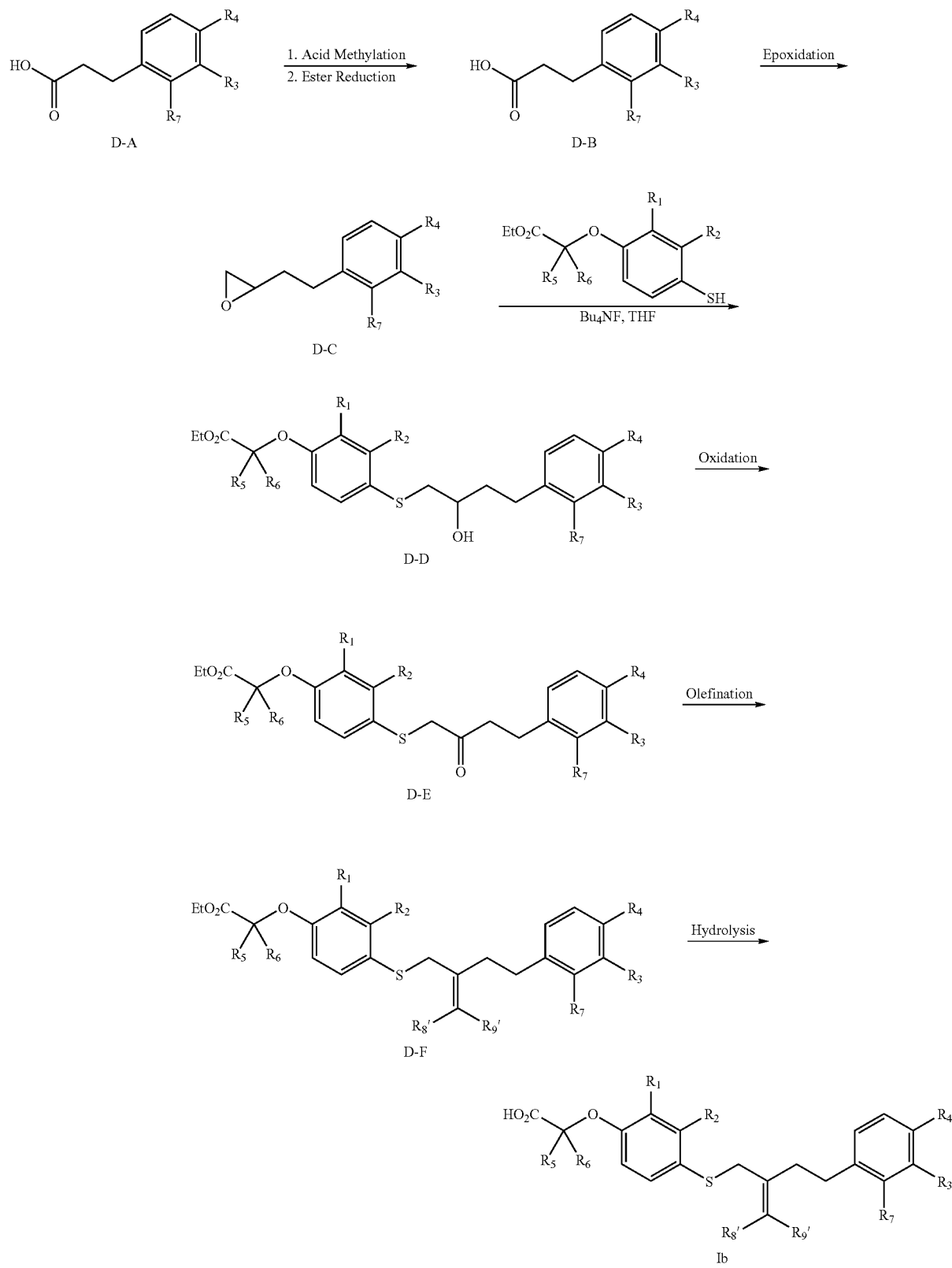

In accordance with Scheme D, wherein $R_8'$ and $R_9'$ are independently selected from H and $C_{1-6}$ alkyl, aldehyde D-B could be prepared in two steps by methylation of acid D-A using (trimethysilyl)diazomethane as a methylating agent followed by reduction of the methyl ester intermediate with a suitable reducing agent such as diisobutylaluminum hydride. Aldehyde D-B is transformed to epoxide D-C by reacting with dimethylsulfonium methylide, which is generated in-situ from treatment of trimethylsulfonium iodide with a strong base such as DMSO anion. Epoxide ring opening of D-C with benzenethiol A-D in the presence of a catalytic amount of tetrabutylammonium fluoride furnishes alcohol D-D, which is oxidized to ketone D-E under mild oxidation conditions by using acetic anhydride and dimethyl sulfoxide. Several types of olefination of ketone D-E may be carried out to provide alkene D-F. For example, Wittig reaction and olefination of D-E with Tebbe reagent will all give D-F. Finally, saponification of ethyl ester D-F under standard conditions gives acid Ib.

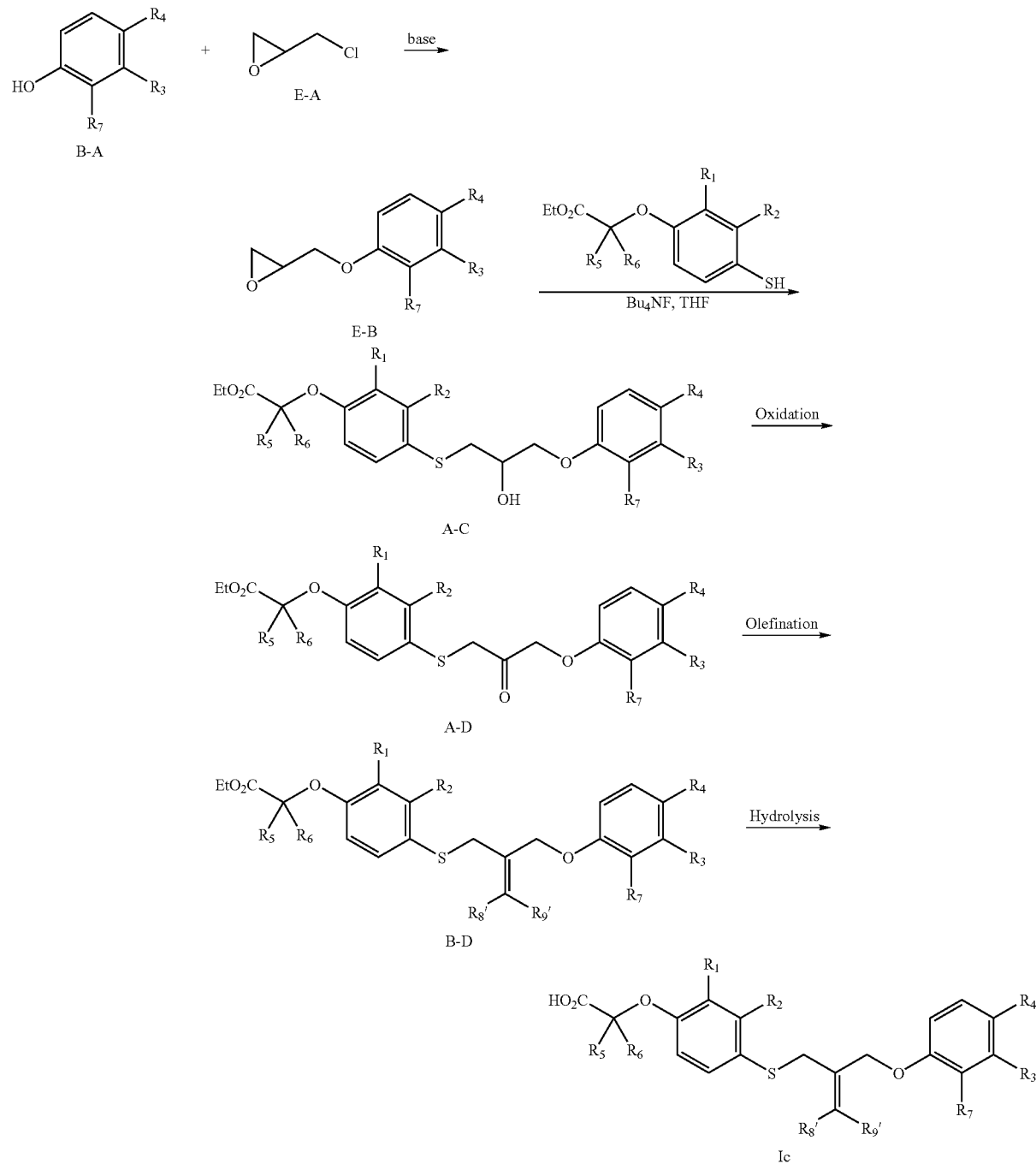

Scheme E

Scheme E shows another route to prepare acid E-E as demonstrated in Scheme B. In Scheme E, epoxide E-B is obtained by treatment of phenol B-A with an appropriate base such as cesium carbonate followed by alkylation with 2-chloromethyl-oxirane E-A. Epoxide ring opening of E-B with benzenethiol A-D, prepared in Scheme A above, in the presence of a catalytic amount of tetrabutylammonium fluoride furnishes alcohol E-C, which is oxidized to ketone E-D under mild oxidation conditions by using acetic anhydride and dimethyl sulfoxide. Several types of olefination of ketone E-D may be carried out to provide alkene B-D. For example, Wittig reaction and olefination of E-D with Tebbe reagent will all give B-D. Finally, saponification of ethyl ester B-D under standard conditions gives acid Ic.

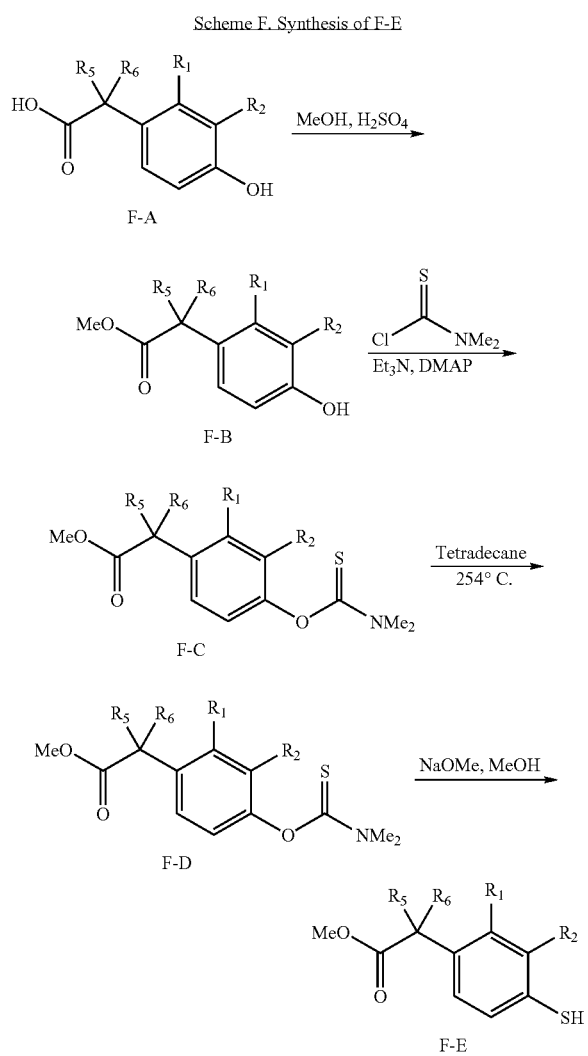

methyl ester F-C by reacting with dimethylthiocarbamoyl chloride in the presence of some appropriate bases such as triethylamine and 4-(dimethylamino)pyridine. At high temperature, in the preferred range of 250 to 300° C., F-C is rearranged to (4-dimethylcarbamoylsulfanylphenyl) acetic acid methyl ester F-D in a high boiling point solvent such as tetradecane. By treatment with a suitable base such as sodium methoxide F-D is transformed to (4-mercaptophenyl) acetic acid methyl ester F-E.

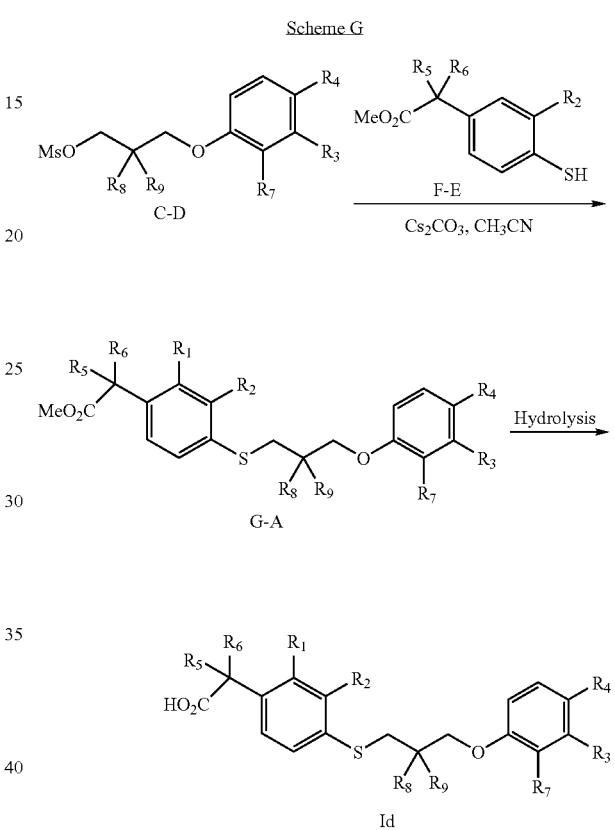

In Scheme G, acetic acid methyl ester G-A is obtained by alkylation of benzenethiol F-E, prepared according to Scheme F above, with mesylate C-D using a suitable base such as $Cs_2CO_3$, $K_2CO_3$, or NaH in an appropriate solvent such as $CH_3CN$ or THF under nitrogen. Under standard saponification conditions methyl ester G-A is hydrolysed to acid Id.

EXAMPLES

Example I

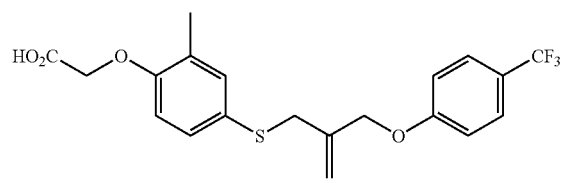

In accordance with Scheme F, (4-hydroxyphenyl) acetic acid F-A, a variety of which are commercially available (such as 3-bromo-4-hydroxyphenyl acetic acid, 3-chloro-4-hydroxyphenyl acetic acid, 3-fluoro-4-hydroxyphenyl acetic acid, 4-hydroxy-3-methoxyphenyl acetic acid, and 4-hydroxy-3-nitrophenyl acetic acid), is methylated to form (4-hydroxyphenyl) acetic acid methyl ester F-B in methanol in the presence of a catalytic amount of a suitable acid such as sulfuric acid or hydrochloric acid. The phenol F-B is converted to (4-dimethylthiocarbamoyloxyphenyl) acetic acid {2-Methyl-4-[2-(4-trifluoromethyl-phenoxymethyl)-allylsulfanyl]-phenoxy}-acetic Acid (4-Chlorosulfonyl-2-methyl-phenoxy)-acetic Acid Ethyl Ester To a flask containing chlorosulfonic acid (15.0 mL, 226 mmol) at 4° C. was added ethyl (2-methylphenoxy)acetate 1-A (10.0 g, 51.6 mmol) slowly. The mixture was stirred at 4° C. for 30 min and room temperature for 2 h, and then poured into ice water. The precipitated white solid was filtered, washed with water, and dried under vacuum overnight to provide 14.0 g (93%) of 1-B as a white solid; $^1$H NMR (300 MHz, CDCl$_3$) δ 7.87-7.84 (m, 2 H), 6.80 (d, J=9.5 Hz, 1 H), 4.76 (s, 2 H), 4.29 (q, J=7.1 Hz, 2 H), 2.37 (s, 3 H), 1.31 (t, J=7.1 Hz, 3 H); MS (ES) m/z: 315 (M+Na$^+$).

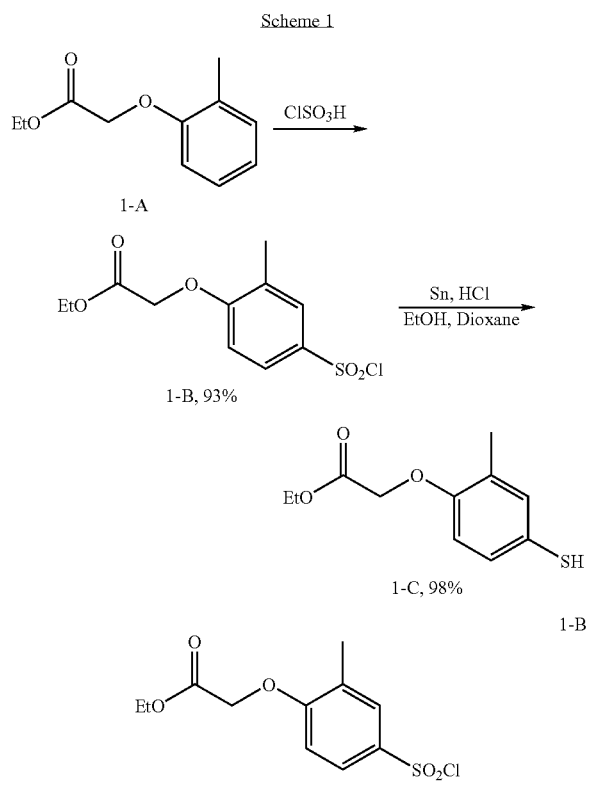

(4-Mercapto-2-methyl-phenoxy)-acetic Acid Ethyl Ester

To a solution of 1-B (4.70 g, 16.1 mmol) in EtOH (20 mL) was added a solution of 4.0 M HCl in dioxane (20 mL) followed by 100 mesh tin powder (9.80 g, 82.6 mmol) portionwise. The mixture was refluxed for 2 h, poured into CH$_2$Cl$_2$/ice (100 mL), and filtered. The filtrate was separated, and the aqueous layer was extracted with CH$_2$Cl$_2$. The combined organic phases were washed with water, dried, and concentrated to give 3.56 g (98%) of 1-C as a yellow oil; $^1$H NMR (300 MHz, CDCl$_3$) δ 7.14-7.03 (m, 2 H), 6.59 (d, J=8.4 Hz, 1 H), 4.60 (s, 2 H), 4.25 (q, J=7.1 Hz, 2 H), 2.24 (s, 3 H), 1.29 (t, J=7.1 Hz, 3 H).

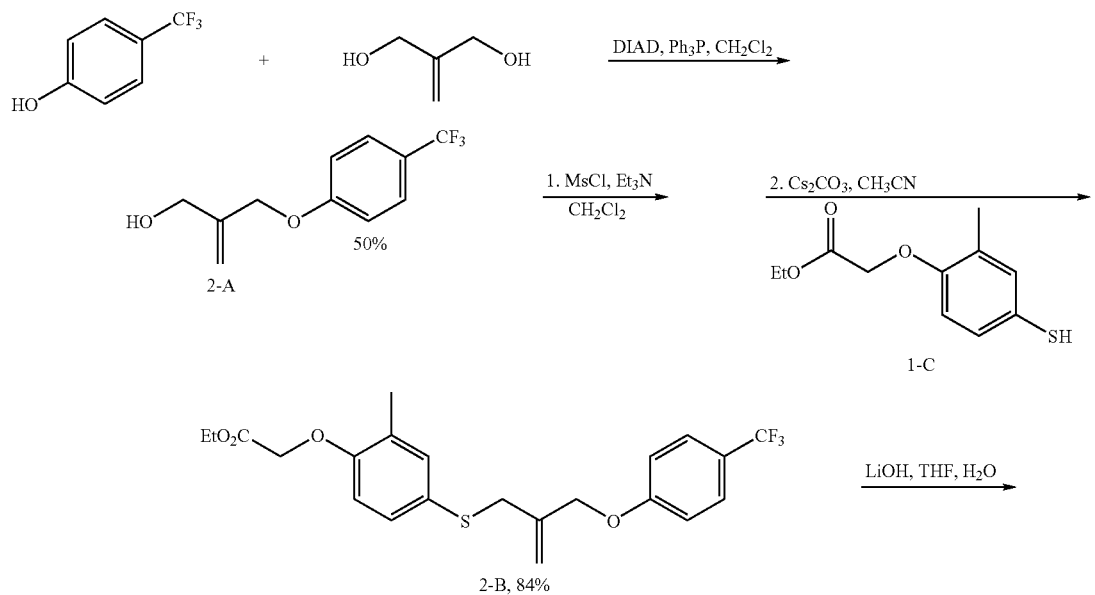

-continued

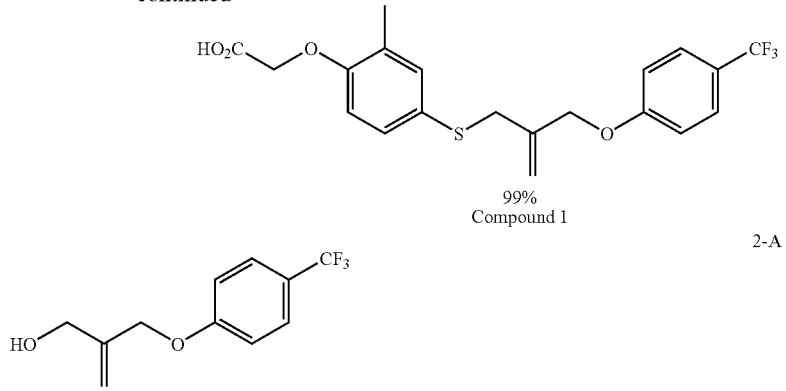

99%
Compound 1

2-(4-Trifluoromethyl-phenoxymethyl)-prop-2-en-1-ol

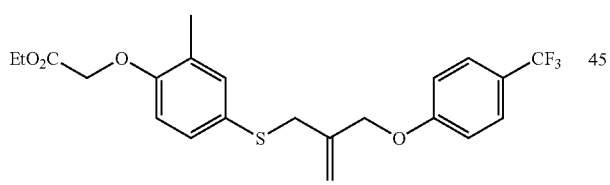
2-A

To a mixture of 4-trifluoromethylphenol (49.0 g, 302 mmol), 2-methylene-1,3-propanediol (40.0 g, 454 mmol), and diisopropyl azodicarboxylate (67.4 g, 333 mmol) in $CH_2Cl_2$ (400 mL) at 0° C. was charged with a solution of triphenylphosphine (87.2 g, 333 mmol) in $CH_2Cl_2$ (400 mL) dropwise. After the mixture was stirred at 0° C. and then allowed to warm up to room temperature overnight, $CH_2Cl_2$ was evaporated under reduced pressure. To the residue was added $Et_2O$ and hexane, and the mixture was cooled to 0° C. The precipitated solid was filtered, and the filtrate was concentrated and column chromatographed (EtOAc/hexane: 1/4) to give 35.2 g (50%) of 2-A; $^1H$ NMR (300 MHz, $CDCl_3$) δ 7.55 (d, J=8.6 Hz, 2 H), 6.99 (d, J=8.6 Hz, 2 H), 5.33 (d, J=0.9 Hz, 1 H), 5.29 (d, J=0.9 Hz, 1 H), 4.65 (s, 2 H), 4.27 (d, J=6.0 Hz, 2 H).

2-B

{2-Methyl-4-[2-(4-trifluoromethyl-phenoxymethyl)-allylsulfanyl]-phenoxy}-acetic Acid Ethyl Ester General Procedure 1 for the Formation of Thioether:

To a solution of 2-A (18.1 g, 78.2 mmol) in $CH_2Cl_2$ (400 mL) at 0° C. were added $Et_3N$ (23.0 mL, 165 mmol) and methanesulfonyl chloride (13.4 g, 117 mmol). The mixture was stirred at 0° C. for 1 h and room temperature overnight and diluted with saturated $NaHCO_3$ (100 mL). The organic layer was separated and the aqueous layer was extracted with $CH_2Cl_2$ (×3). The combined organic phases were dried and concentrated to provide 24.2 g of the crude product.

A mixture of the above crude product, (4-mercapto-2-methyl-phenoxy)acetic acid ethyl ester 1-C (21.2 g, 93.8 mmol), and $Cs_2CO_3$ (76.2 g, 234 mmol) in $CH_3CN$ (290 mL) was stirred at room temperature for 2 h. Water was added and the mixture was extracted with $CH_2Cl_2$. The combined organic layers were dried, concentrated, and column chromatographed (EtOAc/hexane: 1/10) to provide 28.8 g (84%) of 2-B; $^1H$ NMR (300 MHz, $CDCl_3$) δ 7.53 (d, J=8.7 Hz, 2 H), 7.20 (s, 1 H), 7.16 (dd, J=8.4, 2.2 Hz, 1 H), 6.96 (d, J=8.6 Hz, 2 H), 6.59 (d, J=8.4 Hz, 1 H), 5.13 (d, J=0.9 Hz, 1 H), 4.98 (s, 1 H), 4.65 (s, 2 H), 4.60 (s, 2 H), 4.26 (q, J=7.1 Hz, 2 H), 3.56 (s, 2 H), 2.24 (s, 3 H), 1.29 (t, J=7.1 Hz, 3 H); MS (ES) m/z: 463 (M+Na+).

{2-Methyl-4-[2-(4-trifluoromethyl-phenoxymethyl)-allylsulfanyl]-phenoxy}-acetic Acid General Procedure 2 for the Hydrolysis of the Ethyl and Methyl Esters:

To a solution of 2-B (28.8 g, 65.5 mmol) in THF (576 mL) at 0° C. under $N_2$ was added 1.0 M LiOH (131 mL, 131 mmol). After stirring at 0° C. for 45 min and at room temperature for 2.5 h, the mixture was cooled to 0° C., acidified with 1 M HCl, and extracted with EtOAc (×3). The extracts were dried, concentrated, and purified by column chromatography to give 26.7 g (99%) of {2-methyl-4-[2-(4-trifluoromethyl-phenoxymethyl)-allylsulfanyl]-phenoxy}-acetic acid; $^1H$ NMR (300 MHz, $CDCl_3$) δ 7.52 (d, J=8.6 Hz, 2 H), 7.21 (s, 1 H), 7.17 (dd, J=8.4, 2.2 Hz, 1 H), 6.95 (d, J=8.6 Hz, 2 H), 6.62 (d, J=8.4 Hz, 1 H), 5.14 (d, J=1.0 Hz, 1 H), 4.99 (d, J=1.0 Hz, 1 H), 4.65 (s, 4 H), 3.57 (s, 2 H), 2.23 (s, 3 H); MS (ES) m/z: 435 (M+Na+).

Example II

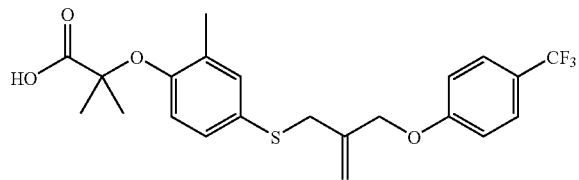

Compound 1

2-Methyl-2-{2-methyl-4-[2-(4-trifluoromethyl-phenoxymethyl)-allylsulfanyl]-phenoxy}-propionic Acid To a solution of 2-bromo-2-methyl-propionic acid ethyl ester (8.27 mL, 64 mmol) and o-methyl-phenol (7.60 g, 70.2 mmol) in dioxane (100 mL) was added $Cs_2CO_3$ (31.25 g, 96 mmol). The mixture was refluxed at 100° C. for 4 hours. After cooling down, the solvent was evaporated under vacuum. The residue was dissolved in ether and then the solution was washed with 1 N NaOH. After drying, the solution was concentrated to give 9.69 g (68%) 3-A; $^1$H NMR (300 MHz, $CDCl_3$) δ 7.13 (d, J=7.3 Hz, 1 H), 7.03 (t, J=7.6 Hz, 1 H), 6.87 (t, J=7.3 Hz, 1 H), 6.66 (d, J=8.2 Hz, 1 H), 4.24 (q, J=7.1 Hz, 2 H), 2.23 (s, 3 H), 1.59 (s, 6 H), 1.25 (t, J=7.1 Hz).

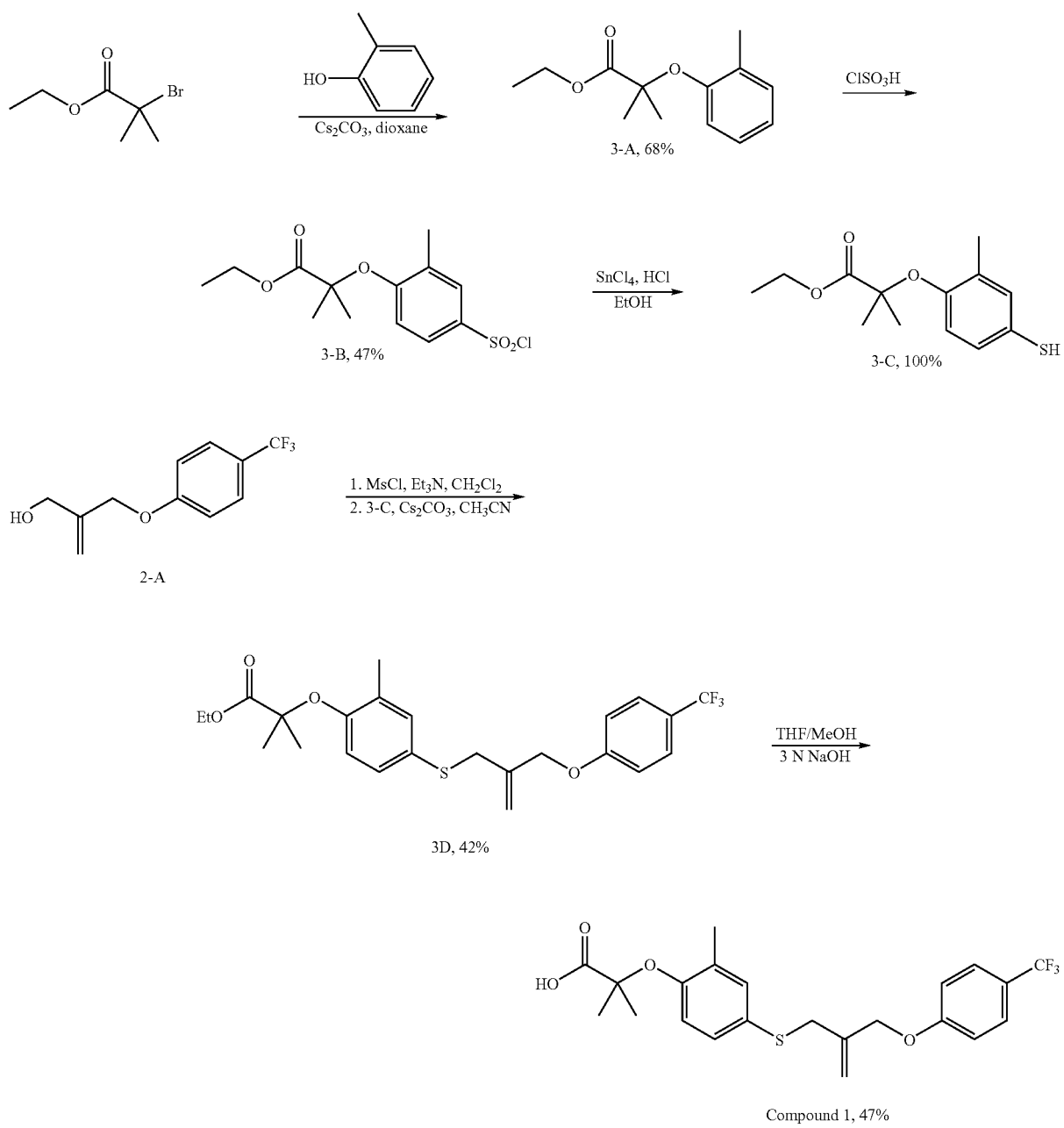

Scheme 3

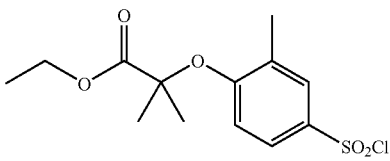

2-(4-Chlorosulfonyl-2-methyl-phenoxy)-2-methyl-propionic Acid Ethyl Ester

ClSO₃H (15.2 mL, 0.229 mol) was slowly added to 3-A (11.3 g, 0.051 mol) at 0° C., The temperature was allowed to warm to room temperature and stir for 1 hour. Upon stirring, the reaction mixture was poured into ice. The solid was filtered and vacuum dried to give 7.7 g (47%) of 3-B; $^1$H NMR (300 MHz, CDCl₃) δ 7.82 (d, J=2.5 Hz, 1 H), 7.75 (dd, J=8.9, 2.5 Hz, 1 H), 6.67 (d, J=8.8 Hz, 1 H), 4.23 (q, J=7.1 Hz, 2 H), 2.31 (s, 3 H), 1.70 (s, 6 H), 1.22 (t, J=7.1 Hz); MS (ES) m/z: 343 (M+Na⁺).

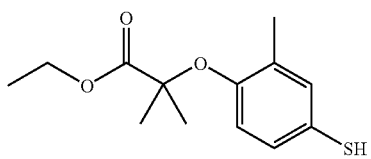

2-(4-Mercapto-2-methyl-phenoxy)-2-methyl-propionic Acid Ethyl Ester

To a solution of 3-B (2.0 g, 6.25 mmol) in EtOH (7.8 mL) was added HCl-dioxane (4 M, 7.8 mL, 31.2 mmol) and tin powder (3.7 g, 31.2 mmol). The mixture was refluxed for 3 hours and then poured into ice. The aqueous solution was extracted with CH₂Cl₂ (50 mL×3). The organic layers were combined and dried over Na₂SO₄. After filtration, the solution was concentrated to give 3.37 g (~100%) 3-C; $^1$H NMR (300 MHz, CDCl₃) δ 7.12 (d, J=2.0 Hz, 1 H), 7.00 (dd, J=8.4, 2.4 Hz, 1 H), 6.56 (d, J=8.4 Hz, 1 H), 4.23 (q, J=7.1 Hz, 2 H), 3.31 (s, 1 H), 2.18 (s, 3 H), 1.57 (s, 6 H), 1.25 (t, J=7.1 Hz); MS (ES) m/z: 255 (M+H⁺).

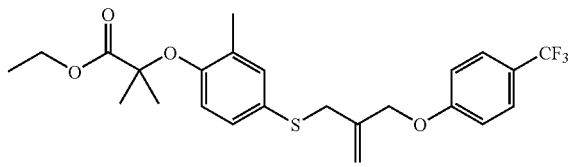

2-Methyl-2-{2-methyl-4-[2-(4-trifluoromethyl-phenoxymethyl)-allylsulfanyl]-phenoxy}-propionic Acid Ethyl Ester To a solution of 2-A (139 mg, 0.6 mmol) in CH₂Cl₂ (3 mL) at 0° C. was added Et₃N (0.18 mL, 1.28 mmol) and then MeSO₂Cl (0.1 g, 0.9 mmol). The mixture was stirred at 0° C. for 10 minutes and then room temperature for 2 hours. After concentration, the crude product was purified by column chromatography (50% CH₂Cl₂ in hexanes) to give 188 mg of crude intermediate.

The above crude intermediate, 3-C (183 mg, 0.72 mmol) and Cs₂CO₃ (469 mg, 1.44 mmol) in acetonitrile was stirred at room temperature for 3 h. Water and Et₂O were added, the organic phase was separated, and the aqueous phase was extracted with Et₂O. The combined organic layers were dried, concentrated and column chromatographed (hexane/EtOAc: 10:1) to provide 140 mg (42%) of 3-D; 1H NMR (300 MHz, CDCl₃) δ 7.52 (d, J=8.6 Hz, 2H), 7.18 (s, 1H), 7.07 (dd, J=8.5, 2.4 Hz, 1H), 6.96 (d, J=8.5 Hz, 2H), 6.57 (d, J=8.5 Hz, 1 H), 5.12 (s, 1H), 4.96 (s, 1H), 4.65 (s, 2H), 4.22 (q, J=7.1 Hz, 2H), 3.56 (s, 2H), 2.17 (s, 3H), 1.58 (s, 6H), 1.28 (t, J=7.1 Hz, 3H); MS (ES) m/z: 491 (M+Na⁺).

Compound 1, 47%

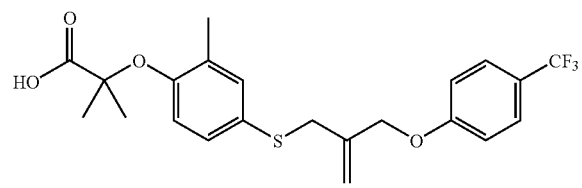

A mixture of 3-D (128 mg, 0.27 mmol), THF (0.7 mL), MeOH (1.4 mL) and 3 N NaOH (0.7 mL) was stirred at 25° C. for 4 h. 1 N HCl and Et₂O were added, the organic phase was separated, and the aqueous phase was extracted with Et₂O. The combined organic layers were dried, concentrated and column chromatographed (CH₂Cl₂/MeOH: 10:1) to provide 57 mg (47%) of Compound 1; $^1$H NMR (300 MHz, CDCl₃) δ 7.52 (d, J=8.6 Hz, 2H), 7.20 (d, J=1.8 Hz, 1 H), 7.11 (dd, J=8.4, 2.0 Hz, 1H), 6.96 (d, J=8.6 Hz, 2H), 6.73 (d, J=8.4 Hz, 1H), 5.15 (s, 1H), 5.02 (s, 1H), 4.65 (s, 2H), 3.59 (s, 2H), 2.18 (s, 3H), 1.59 (s, 6H)); MS (ES) m/z: 439 (M−H⁺).

D. Formulation and Administration

The present compounds are PPAR delta agonists and are therefore useful in treating or inhibiting the progression of PPAR delta mediated conditions, such as diabetes, cardiovascular diseases, Metabolic X Syndrome, hypercholesterolemia, hypo-HDL-cholesterolemia, hyper-LDL-cholesterolemia, dyslipidemia, atherosclerosis, obesity, and complications thereof. For instance, complications of diabetes include such conditions as neuropathy, nephropathy, and retinopathy.

The invention features a method for treating a subject with a PPAR delta mediated disease, said method comprising administering to the subject a therapeutically effective amount of a pharmaceutical composition comprising a compound of the invention. The invention also provides a method for treating or inhibiting the progression of diabetes or impaired glucose tolerance in a subject, wherein the method comprises administering to the subject a therapeutically effective amount of a pharmaceutical composition comprising a compound of the invention.

The compounds of the present invention may be formulated into various pharmaceutical forms for administration purposes. To prepare these pharmaceutical compositions, an effective amount of a particular compound, in base or acid addition salt form, as the active ingredient is intimately mixed with a pharmaceutically acceptable carrier.

A carrier may take a wide variety of forms depending on the form of preparation desired for administration. These pharmaceutical compositions are desirably in unitary dosage form suitable, preferably, for oral administration or parenteral injection. For example, in preparing the compositions in oral dosage form, any of the usual pharmaceutical media may be employed. These include water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. In view of their ease in administration, tablets and capsules represent the most advantageous oral dosage unit form, in which case solid pharmaceutical carriers are generally employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Such additives may facilitate the administration to the skin and/or may be helpful for preparing the desired compositions. These compositions may be administered in various ways, e.g., as a transdermal patch, as a spot-on, as an ointment. Acid addition salts of the compounds of formula I, due to their increased water solubility over the corresponding base form, are more suitable in the preparation of aqueous compositions.

It is especially advantageous to formulate the aforementioned pharmaceutical compositions in dosage unit form for ease of administration and uniformity of dosage. Dosage unit form as used in the specification herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Pharmaceutically acceptable acid addition salts include the therapeutically active non-toxic acid addition salts of disclosed compounds. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, palmoic and the like acids. The term addition salt also comprises the solvates which the disclosed compounds, as well as the salts thereof, are able to form. Such solvates are for example hydrates, alcoholates and the like. Conversely the salt form can be converted by treatment with alkali into the free base form.

Stereoisomeric forms define all the possible isomeric forms which the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the (R)- or (S)-configuration; substituents on bivalent cyclic saturated radicals may have either the cis- or trans-configuration. The invention encompasses stereochemically isomeric forms including diastereoisomers, as well as mixtures thereof in any proportion of the disclosed compounds. The disclosed compounds may also exist in their tautomeric forms. Such forms although not explicitly indicated in the above and following formulae are intended to be included within the scope of the present invention.

Those of skill in the treatment of disorders or conditions mediated by the PPAR delta could easily determine the effective daily amount from the test results presented hereinafter and other information. In general it is contemplated that a therapeutically effective dose would be from 0.001 mg/kg to 5 mg/kg body weight, more preferably from 0.01 mg/kg to 0.5 mg/kg body weight. It may be appropriate to administer the therapeutically effective dose as two, three, four or more sub-doses at appropriate intervals throughout the day. Said sub-doses may be formulated as unit dosage forms, for example, containing 0.05 mg to 250 mg or 750 mg, and in particular 0.5 to 50 mg of active ingredient per unit dosage form. Examples include 2 mg, 4 mg, 7 mg, 10 mg, 15 mg, 25 mg, and 35 mg dosage forms. Compounds of the invention may also be prepared in time-release or subcutaneous or transdermal patch formulations. Disclosed compound may also be formulated as a spray or other topical or inhalable formulations.

The exact dosage and frequency of administration depends on the particular compound of Formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines.

The next section includes detailed information relating to the use of the disclosed compounds and compositions.

E. Use

The compounds of the present invention are pharmaceutically active, for example, as PPAR delta agonists and preferably as PPAR alpha/delta dual agonists. According to one aspect of the invention, the compounds are preferably selective PPAR delta agonists, having an activity index (e.g., PPAR delta potency over PPAR alpha/gamma potency) of 10 or more, and preferably 15, 25, 30, 50 or 100 or more. According to another aspect, the compounds are dual PPAR alpha and PPAR delta agonists.

According to the invention, the disclosed compounds and compositions are useful for the amelioration of symptoms associated with, the treatment of, and the prevention of, the following conditions and diseases: phase I hyperlipidemia, pre-clinical hyperlipidemia, phase II hyperlipidemia, hypertension, CAD (coronary artery disease), atherosclerosis, coronary heart disease, cardiovascular disease, hypercholesteremia, and hypertriglyceridemia, type II diabetes, insulin resistance, impaired glucose tolerance, dyslipidemia, and low HDL-C. Preferred compounds of the invention are useful in lowering serum levels of low-density lipoproteins (LDL), intermediate density lipoprotein (IDL), and/or small-density LDL and other atherogenic molecules, or molecules that cause atherosclerotic complications, thereby reducing cardiovascular complications. Preferred compounds also are useful in elevating serum levels of high-density lipoproteins (HDL), in lowering serum levels of triglycerides, LDL, and/or free fatty acids. It is also desirable to lower fasting plasma glucose (FPG)/HbA1c.

PPAR alpha-mediated diseases include Syndrome X (or Metabolic Syndrome), dyslipidemia, high blood pressure, obesity, insulin resistance, impaired fasting glucose, type II diabetes, atherosclerosis, non-alcoholic steatohepatitis, hypercholesterolemia, hypertriglyceridemia, and low HDL-C.

According to one aspect of the invention, the disclosed compounds may be used in a method for treating or inhibiting the progression of a PPAR-delta mediated condition and, optionally, an additional PPAR-alpha mediated condition, said method comprising administering to a patient in need of treatment a pharmaceutically effective amount of a composition of the invention. Another aspect of the invention is a method of use wherein the PPAR-delta mediated condition is selected from hyperlipidemia, atherosclerosis, cardiovascular disease, hypercholesteremia, type II diabetes, insulin resistance, and impaired glucose tolerance, and other conditions disclosed herein; and a PPAR-alpha mediated condition is selected from Syndrome X (or Metabolic Syndrome), dyslipidemia, high blood pressure, obesity, and impaired fasting glucose, insulin resistance, type II diabetes and other conditions disclosed herein.

A further aspect of the invention is a method for treating at least one PPAR-delta mediated condition and at least one PPAR-alpha mediated condition in a patient, said method comprising administering to a patient in need of treatment a pharmaceutically effective amount of a composition of the invention.

The invention also features pharmaceutical compositions which include, without limitation, one or more of the disclosed compounds, and pharmaceutically acceptable carrier or excipient.

1. Dosages

Those skilled in the art will be able to determine, according to known methods, the appropriate dosage for a patient, taking into account factors such as age, weight, general health, the type of symptoms requiring treatment, and the presence of other medications. In general, an effective amount will be between 0.1 and 1000 mg/kg per day, preferably between 1 and 300 mg/kg body weight, and daily dosages will be between 10 and 5000 mg for an adult subject of normal weight. Capsules, tablets or other formulations (such as liquids and film-coated tablets) may be of between 5 and 200 mg, such as 10, 15, 25, 35, 50 mg, 60 mg, and 100 mg and can be administered according to the disclosed methods.

2. Formulations

Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

3. Combination Therapy

The compounds of the present invention may be used in combination with other pharmaceutically active agents. These agents include lipid lowering agents, and blood pressure lowering agents such as statin drugs and the fibrates.

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

Anti-diabetic agents include thiazolidinedione and non-thiazolidinedione insulin sensitizers, which decrease peripheral insulin resistance by enhancing the effects of insulin at target organs and tissues.

Some of the following agents are known to bind and activate the nuclear receptor peroxisome proliferator-activated receptor-gamma (PPARγ) which increases transcription of specific insulin-responsive genes. Examples of PPAR-gamma agonists are thiazolidinediones such as:

(1) rosiglitazone (2,4-thiazolidinedione, 5-((4-(2-(methyl-2-pyridinylamino)ethoxy)phenyl)methyl)-, (Z)-2-butenedioate (1:1) or 5-((4-(2-(methyl-2-pyridinylamino)ethoxy)phenyl)methyl)-2,4-thiazolidinedione, known as AVANDIA; also known as BRL 49653, BRL 49653C, BRL 49653c, SB 210232, or rosiglitazone maleate);

(2) pioglitazone (2,4-thiazolidinedione, 5-((4-(2-(5-ethyl-2-pyridinyl)ethoxy)phenyl)methyl)-, monohydrochloride, (+−)- or 5-((4-(2-(5-ethyl-2-pyridyl)ethoxy)phenyl)methy)-2,4-thiazolidinedione, known as ACTOS, ZACTOS, or GLUSTIN; also known as AD 4833, U 72107, U 72107A, U 72107E, pioglitazone hydrochloride (USAN));

(3) troglitazone (5-((4-((3,4-dihydro-6-hydroxy-2,5,7,8-tetramethyl-2H-1-benzopyran-2-yl)methoxy)phenyl) methyl)-2,4-thiazolidinedione, known as NOSCAL, REZULIN, ROMOZIN, or PRELAY; also known as CI 991, CS 045, GR 92132, GR 92132X);

(4) isaglitazone ((+)-5-[[6-[(2-fluorophenyl)methoxy]-2-naphthalenyl]methyl]-2,4-thiazolidinedione or 5-((6-((2-fluorophenyl)methoxy)-2-naphthalenyl)methyl-2, 4-thiazolidinedione or 5-(6-(2-fluorobenzyloxy) naphthalen-2-ylmethyl)thiazolidine-2,4-dione, also known as MCC-555 or neoglitazone); and (5) 5-BTZD.

Additionally, the non-thiazolidinediones that act as insulin sensitizing agents include, but are not limited to:

(1) JT-501 (JTT 501, PNU-1827, PNU-716-MET-0096, or PNU 182716: isoxazolidine-3,5-dione, 4-((4-(2-phenyl-5-methyl)-1,3-oxazolyl)ethylphenyl-4)methyl-);

(2) KRP-297 (5-(2,4-dioxothiazolidin-5-ylmethyl)-2-methoxy-N-(4-(trifluoromethyl)benzyl)benzamide or 5-((2,4-dioxo-5-thiazolidinyl)methyl)-2-methoxy-N-((4-(trifluoromethyl)phenyl)methyl)benzamide); and (3) Farglitazar (L-tyrosine, N-(2-benzoylphenyl)-o-(2-(5-methyl-2-phenyl-4-oxazolyl)ethyl)- or N-(2-benzoylphenyl)-O-(2-(5-methyl-2-phenyl-4-oxazolyl) ethyl)-L-tyrosine, or GW2570 or GI-262570).

Other agents have also been shown to have PPAR modulator activity such as PPAR gamma, SPPAR gamma, and/or PPAR delta/gamma agonist activity. Examples are listed below:

(1) AD 5075;
(2) R 119702 ((+−)-5-(4-(5-Methoxy-1H-benzimidazol-2-ylmethoxy)benzyl)thiazolin-2,4-dione hydrochloride, or CI 1037 or CS 011);
(3) CLX-0940 (peroxisome proliferator-activated receptor alpha agonist/peroxisome proliferator-activated receptor gamma agonist);
(4) LR-90 (2,5,5-tris(4-chlorophenyl)-1,3-dioxane-2-carboxylic acid, PPARdelta/γ agonist);
(5) Tularik (PPARγ agonist);
(6) CLX-0921 (PPARγ agonist);
(7) CGP-52608 (PPAR agonist);
(8) GW-409890 (PPAR agonist);
(9) GW-7845 (PPAR agonist);
(10) L-764406 (PPAR agonist);
(11) LG-101280 (PPAR agonist);
(12) LM-4156 (PPAR agonist);
(13) Risarestat (CT-112);
(14) YM 440 (PPAR agonist);
(15) AR-H049020 (PPAR agonist);
(16) GW 0072 (4-(4-((2S,5S)-5-(2-(bis(phenylmethyl) amino)-2-oxoethyl)-2-heptyl-4-oxo-3-thiazolidinyl) butyl)benzoic acid);
(17) GW 409544 (GW-544 or GW-409544);
(18) NN 2344 (DRF 2593);
(19) NN 622 (DRF 2725);
(20) AR-H039242 (AZ-242);
(21) GW 9820 (fibrate);
(22) GW 1929 (N-(2-benzoylphenyl)-O-(2-(methyl-2-pyridinylamino)ethyl)-L-tyrosine, known as GW 2331, PPAR alpha/γ agonist);
(23) SB 219994 ((S)-4-(2-(2-benzoxazolylmethylamino) ethoxy)-alpha-(2,2,2-trifluoroethoxy)benzene propanoic acid or 3-(4-(2-(N-(2-benzoxazolyl)-N-methylamino)ethoxy)phenyl)-2(S)-(2,2,2-trifluoroethoxy) propionic acid or benzenepropanoic acid, 4-(2-(2-benzoxazolylmethylamino)ethoxy)-alpha-(2,2,2-trifluoroethoxy)-, (alphaS)-, PPARalpha/γ agonist);
(24) L-796449 (PPAR alpha/γ agonist);
(25) Fenofibrate (Propanoic acid, 2-[4-(4-chlorobenzoyl) phenoxy]-2-methyl-, 1-methylethyl ester, known as TRICOR, LIPCOR, LIPANTIL, LIPIDIL MICRO PPAR alpha agonist);
(26) GW-9578 (PPAR alpha agonist);
(27) GW-2433 (PPAR alpha/γ agonist);
(28) GW-0207 (PPARγ agonist);
(29) LG-100641 (PPARγ agonist);
(30) LY-300512 (PPARγ agonist);
(31) NID525-209 (NID-525);
(32) VDO-52 (VDO-52);
(33) LG 100754 (peroxisome proliferator-activated receptor agonist);
(34) LY-510929 (peroxisome proliferator-activated receptor agonist);
(35) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455); and
(36) GW-1536 (PPAR alpha/γ agonist).

(B) Other insulin sensitizing agents include, but are not limited to:

(1) INS-1 (D-chiro inositol or D-1,2,3,4,5,6-hexahydroxycyclohexane);
(2) protein tyrosine phosphatase 1 B (PTP-1B) inhibitors;
(3) glycogen synthase kinase-3 (GSK3) inhibitors;
(4) beta 3 adrenoceptor agonists such as ZD 2079 ((R)-N-(2-(4-(carboxymethyl)phenoxy)ethyl)-N-(2-hydroxy-2-phenethyl) ammonium chloride, also known as ICI D 2079) or AZ 40140;
(5) glycogen phosphorylase inhibitors;
(6) fructose-1,6-bisphosphatase inhibitors;
(7) chromic picolinate, vanadyl sulfate (vanadium oxysulfate);
(8) KP 102 (organo-vanadium compound);
(9) chromic polynicotinate;
(10) potassium channel agonist NN 414;
(11) YM 268 (5,5'-methylene-bis(1,4-phenylene)bismethylenebis(thiazolidine-2,4-dione);
(12) TS 971;
(13) T 174 ((+−)-5-(2,4-dioxothiazolidin-5-ylmethyl)-2-(2-naphthylmethyl)benzoxazole);
(14) SDZ PGU 693 ((+)-trans-2(S-((4-chlorophenoxy)methyl)-7alpha-(3,4-dichlorophenyl)tetrahydropyrrolo(2, 1-b)oxazol-5(6H)-one);
(15) S 15261 ((−)-4-(2-((9H-fluoren-9-ylacetyl)amino) ethyl) benzoic acid 2-((2-methoxy-2-(3-(trifluoromethyl)phenyl)ethyl)amino)ethyl ester);
(16) AZM 134 (Alizyme);
(17) ARIAD;
(18) R 102380;
(19) PNU 140975 (1-(hydrazinoiminomethyl)hydrazino) acetic acid;
(20) PNU 106817 (2-(hydrazinoiminomethyl)hydrazino) acetic acid;
(21) NC 2100 (5-((7-(phenylmethoxy)-3-quinolinyl)methyl)-2,4-thiazolidinedione;
(22) MXC 3255;
(23) MBX 102;
(24) ALT 4037;
(25) AM 454;

(26) JTP 20993 (2-(4-(2-(5-methyl-2-phenyl-4-oxazolyl)ethoxy)benzyl)-malonic acid dimethyl diester);
(27) Dexlipotam (5(R)-(1,2-dithiolan-3-yl)pentanoic acid, also known as (R)-alpha lipoic acid or (R)-thioctic acid);
(28) BM 170744 (2,2-Dichloro-12-(p-chlorophenyl)dodecanoic acid);
(29) BM 152054 (5-(4-(2-(5-methyl-2-(2-thienyl)oxazol-4-yl)ethoxy)benzothien-7-ylmethyl)thiazolidine-2,4-dione);
(30) BM 131258 (5-(4-(2-(5-methyl-2-phenyloxazol-4-yl)ethoxy)benzothien-7-ylmethyl)thiazolidine-2,4-dione);
(31) CRE 16336 (EML 16336);
(32) HQL 975 (3-(4-(2-(5-methyl-2-phenyloxazol-4-yl)ethoxy)phenyl)-2(S)-(propylamino)propionic acid);
(33) DRF 2189 (5-((4-(2-(1-Indolyl)ethoxy)phenyl)methyl)thiazolidine-2,4-dione);
(34) DRF 554158;
(35) DRF-NPCC;
(36) CLX 0100, CLX 0101, CLX 0900, or CLX 0901;
(37) IkappaB Kinase (IKK B) Inhibitors
(38) mitogen-activated protein kinase (MAPK) inhibitors p38 MAPK Stimulators
(39) phosphatidyl-inositide triphosphate
(40) insulin recycling receptor inhibitors
(41) glucose transporter 4 modulators
(42) TNF-α antagonists
(43) plasma cell differentiation antigen-1 (PC-1) Antagonists
(44) adipocyte lipid-binding protein (ALBP/aP2) inhibitors
(45) phosphoglycans
(46) Galparan;
(47) Receptron;
(48) islet cell maturation factor;
(49) insulin potentiating factor (IPF or insulin potentiating factor-1);
(50) somatomedin C coupled with binding protein (also known as IGF-BP3, IGF-BP3, SomatoKine);
(51) Diab II (known as V-411) or Glucanin, produced by Biotech Holdings Ltd. or Volque Pharmaceutical;
(52) glucose-6 phosphatase inhibitors;
(53) fatty acid glucose transport protein;
(54) glucocorticoid receptor antagonists; and
(55) glutamine:fructose-6-phosphate amidotransferase (GFAT) modulators.

(C) Biguanides, which decrease liver glucose production and increases the uptake of glucose. Examples include metformin such as:
(1) 1,1-dimethylbiguanide (e.g., Metformin—DepoMed, Metformin—Biovail Corporation, or METFORMIN GR (metformin gastric retention polymer)); and
(2) metformin hydrochloride (N,N-dimethylimidodicarbonimidic diamide monohydrochloride, also known as LA 6023, BMS 207150, GLUCOPHAGE, or GLUCOPHAGE XR.

(D) Alpha-glucosidase inhibitors, which inhibit alpha-glucosidase. Alpha-glucosidase converts fructose to glucose, thereby delaying the digestion of carbohydrates. The undigested carbohydrates are subsequently broken down in the gut, reducing the post-prandial glucose peak. Examples include, but are not limited to:
(1) acarbose (D-glucose, O-4,6-dideoxy-4-(((1S-(1alpha,4alpha,5beta,6alpha))-4,5,6-trihydroxy-3-(hydroxymethyl)-2-cyclohexen-1-yl)amino)-alpha-D-glucopyranosyl-(1-4)-O-alpha-D-glucopyr also known as AG-5421, Bay-g-542, BAY-g-542, GLUCOBAY, PRECOSE, GLUCOR, PRANDASE, GLUMIDA, or ASCAROSE);
(2) Miglitol (3,4,5-piperidinetriol, 1-(2-hydroxyethyl)-2-(hydroxymethyl) -, (2R(2alpha,3beta,4alpha,5beta))- or (2R,3R,4R,5S)-1-(2-hydroxyethyl)-2-(hydroxymethyl)-3,4,5-piperidinetriol, also known as BAY 1099, BAY M 1099, BAY-m-1099, BAYGLITOL, DIASTABOL, GLYSET, MIGLIBAY, MITOLBAY, PLUMAROL);
(3) CKD-711 (0-4-deoxy-4-((2,3-epoxy-3-hydroxymethyl-4,5,6-trihydroxycyclohexane-1-yl)amino)-alpha-b-glucopyranosyl-(1-4)-alpha-D-glucopyranosyl-(1-4)-D-glucopyranose);
(4) emiglitate (4-(2-((2R,3R,4R,5S)-3,4,5-trihydroxy-2-(hydroxymethyl)-1-piperidinyl)ethoxy)benzoic acid ethyl ester, also known as BAY o 1248 or MKC 542);
(5) MOR 14 (3,4,5-piperidinetriol, 2-(hydroxymethyl)-1-methyl-, (2R-(2alpha,3beta,4alpha,5beta))-, also known as N-methyldeoxynojirimycin or N-methylmoranoline); and
(6) Voglibose (3,4-dideoxy-4-((2-hydroxy-1-(hydroxymethyl)ethyl)amino)-2-C-(hydroxymethyl)-D-epi-inositol or D-epi-Inositol,3,4-dideoxy-4-((2-hydroxy-1-(hydroxymethyl)ethyl)amino)-2-C-(hydroxymethyl)-, also known as A 71100, AO 128, BASEN, GLUSTAT, VOGLISTAT.

(E) Insulins include regular or short-acting, intermediate-acting, and long-acting insulins, non-injectable or inhaled insulin, tissue selective insulin, glucophosphokinin (D-chiroinositol), insulin analogues such as insulin molecules with minor differences in the natural amino acid sequence and small molecule mimics of insulin (insulin mimetics), and endosome modulators. Examples include, but are not limited to:
(1) Biota;
(2) LP 100;
(3) (SP-5-21)-oxobis(1-pyrrolidinecarbodithioato-S,S') vanadium,
(4) insulin aspart (human insulin (28B-L-aspartic acid) or B28-Asp-insulin, also known as insulin X14, INA-X14, NOVORAPID, NOVOMIX, or NOVOLOG);
(5) insulin detemir (Human 29B-(N6-(1-oxotetradecyl)-L-lysine)-(1A-21A), (1B-29B)-Insulin or NN 304);
(6) insulin lispro ("28B-L-lysine-29B-L-proline human insulin, or Lys(B28), Pro(B29) human insulin analog, also known as lys-pro insulin, LY 275585, HUMALOG, HUMALOG MIX 75/25, or HUMALOG MIX 50/50);
(7) insulin glargine (human (A21-glycine, B31-arginine, B32-arginine) insulin HOE 901, also known as LANTUS, OPTISULIN);
(8) Insulin Zinc Suspension, extended (Ultralente), also known as HUMULIN U or ULTRALENTE;
(9) Insulin Zinc suspension (Lente), a 70% crystalline and 30% amorphous insulin suspension, also known as LENTE ILETIN II, HUMULIN L, or NOVOLIN L;
(10) HUMULIN 50/50 (50% isophane insulin and 50% insulin injection);
(11) HUMULIN 70/30 (70% isophane insulin NPH and 30% insulin injection), also known as NOVOLIN 70/30, NOVOLIN 70/30 PenFill, NOVOLIN 70/30 Prefilled;
(12) insulin isophane suspension such as NPH ILETIN II, NOVOLIN N, NOVOLIN N PenFill, NOVOLIN N Prefilled, HUMULIN N;

(13) regular insulin injection such as ILETIN II Regular, NOVOLIN R, VELOSULIN BR, NOVOLIN R PenFill, NOVOLIN R Prefilled, HUMULIN R, or Regular U-500 (Concentrated);
(14) ARIAD;
(15) LY 197535;
(16) L-783281; and
(17) TE-17411.
(F) Insulin secretion modulators such as:
(1) glucagon-like peptide-1(GLP-1) and its mimetics;
(2) glucose-insulinotropic peptide (GIP) and its mimetics;
(3) exendin and its mimetics;
(4) dipeptyl protease (DPP or DPPIV) inhibitors such as
  (4a) DPP-728 or LAF 237 (2-pyrrolidinecarbonitrile, 1-(((2-((5-cyano-2-pyridinyl)amino)ethyl)amino)acetyl), known as NVP-DPP-728, DPP-728A, LAF-237);
  (4b) P 3298 or P32/98 (di-(3N-((2S,3S)-2-amino-3-methyl-pentanoyl)-1,3-thiazolidine)fumarate);
  (4c) TSL 225 (tryptophyl-1,2,3,4-tetrahydroisoquinoline-3-carboxylic acid);
  (4d) Valine pyrrolidide (valpyr);
  (4e) 1-aminoalkylisoquinolinone-4-carboxylates and analogues thereof;
  (4f) SDZ 272-070 (1-(L-Valyl)pyrrolidine);
  (4g) TMC-2A, TMC-2B, or TMC-2C;
  (4h) Dipeptide nitriles (2-cyanopyrrolodides);
  (4i) CD26 inhibitors; and
  (4j) SDZ 274-444;
(5) glucagon antagonists such as AY-279955; and
(6) amylin agonists which include, but are not limited to, pramlintide (AC-137, Symlin, tripro-amylin or pramlintide acetate).

The present compounds may also increase insulin sensitivity with little or no increase in body weight than that found with the use of existing PPAR gamma agonists. Oral anti-diabetic agents may include insulin, sulfonylureas, biguanides, meglitinides, AGI's, PPAR alpha agonists, and PPAR gamma agonists, and dual PPAR alpha/gamma agonists.

The present compounds also may increase fat and/or lipid metabolism, providing a method for losing weight, losing fat weight, lowering body mass index, lowering lipids (such as lowering triglycerides), or treating obesity or the condition of being overweight. Examples of lipid lowering agents include bile acid sequestrants, fibric acid derivatives, nicotinic acid, and HMGCoA reductase inhibitors. Specific examples include statins such as LIPITOR®, ZOCOR®, PRAVACHOL®, LESCOL®, and MEVACOR®, and pitavastatin (nisvastatin) (Nissan, Kowa Kogyo, Sankyo, Novartis) and extended release forms thereof, such as ADX-159 (extended release lovastatin), as well as Colestid, Locholest, Questran, Atromid, Lopid, and Tricor.

Examples of blood pressure lowering agents include antihypertensive agents, such as angiotensin-converting enzyme (ACE) inhibitors (Accupril, Altace, Captopril, Lotensin, Mavik, Monopril, Prinivil, Univasc, Vasotec, and Zestril), adrenergic blockers (such as Cardura, Dibenzyline, Hylorel, Hytrin, Minipress, and Minizide) alpha/beta adrenergic blockers (such as Coreg, Normodyne, and Trandate), calcium channel blockers (such as Adalat, Calan, Cardene, Cardizem, Covera-HS, Dilacor, DynaCirc, Isoptin, Nimotop, Norvace, Plendil, Procardia, Procardia XL, Sula, Tiazac, Vascor, and Verelan), diuretics, angiotensin II receptor antagonists (such as Atacand, Avapro, Cozaar, and Diovan), beta adrenergic blockers (such as Betapace, Blocadren, Brevibloc, Cartrol, Inderal, Kerlone, Lavatol, Lopressor, Sectral, Tenormin, Toprol-XL, and Zebeta), vasodilators (such as Deponit, Dilatrate, SR, Imdur, Ismo, Isordil, Isordil Titradose, Monoket, Nitro-Bid, Nitro-Dur, Nitrolingual Spray, Nitrostat, and Sorbitrate), and combinations thereof (such as Lexxel, Lotrel, Tarka, Teczem, Lotensin HCT, Prinzide, Uniretic, Vaseretic, Zestoretic).

F. Biological Examples

Transfection Assay Method for PPAR Receptors

HEK293 cells were grown in DMEM/F12 medium supplemented with 10% FBS and glutamine (Invitrogen) and incubated in a 5% $CO_2$ incubator at 37° C. The cells were co-transfected using DMRIE-C reagent (Invitrogen) in serum free medium (Opti-MEM, Invitrogen) with two mammalian expression plasmids, one containing the DNA sequence coding for the ligand binding domains of either PPARα, γ or δ fused to the yeast GAL4 DNA binding domain and the other containing the promoter sequence of the yeast GAL4 (UAS) fused to the firefly luciferase cDNA reporter. The next day, the medium was changed to DMEM/F12 medium supplemented with 5% charcoal treated serum (Hyclone) and glutamine. After 6 hrs the cells were trypsinized and seeded at a density of 50,000 cells/well into 96 well plates and incubated overnight as above. The cells were then treated with test compounds or vehicle and incubated for 18-24 hrs as above. Luciferase reporter activity was measured using the Steady-Glo Luciferase Assay Kit from Promega. DMRIE-C Reagent was purchased from GIBCO Cat. No. 10459-014. OPTI-MEM I Reduced Serum Medium was purchased from GIBCO (Cat. No. 31985). Steady-Glo Luciferase Assay Kit was purchased from Promega (Part# E254B).

A variety of example compounds have been made and tested, with a range of in vitro results. Below are representative compounds and data; in some cases, where multiple $EC_{50}$'s are shown, multiple measurements were taken. Naturally, different compounds in Formula (I) may have not have activities identical to any one compound below.

TABLE 2

| | In Vitro Data | | |
|---|---|---|---|
| Compound Number | $EC_{50}$ (PPAR delta) nM | $EC_{50}$ (PPAR gamma) nM | $EC_{50}$ (PPAR alpha) nM |
| 2 | 41.5 | 899 | 900 |

G. Other Embodiments

The features and principles of the invention are illustrated in the discussion, examples, and claims herein. Various adaptations and modifications of the invention will be apparent to a person of ordinary skill in the art and such other embodiments are also within the scope of the invention. Publications cited herein are incorporated in their entirety by reference.

The invention claimed is:
1. A compound of Formula (I):

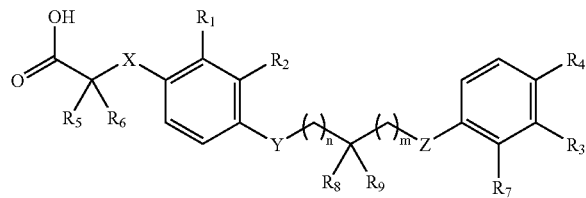

wherein
X is selected from a covalent bond, S, and O;
Y is S or O;
Z is O or $CH_2$, provided when Y is O, then Z is O;
$R_1$ and $R_2$ are independently selected from H, $C_{1-3}$ alkyl, $C_{1-3}$ alkoxy, halo, and $NR_aR_b$ wherein $R_a$ and $R_b$ are independently H or $C_{1-3}$ alkyl;
$R_3$ and $R_4$ are independently selected from H, halo, cyano, $C_{1-5}$ alkyl, hydroxy, $C_{2-4}$ acyl, $C_{1-4}$ alkoxy, and $NR_cR_d$ wherein $R_c$ and $R_d$ are independently H or $C_{1-3}$ alkyl, provided that $R_3$ and $R_4$ are not both H;
$R_5$ and $R_6$ are independently selected from H, $C_{1-8}$ alkyl and substituted $C_{1-8}$ alkyl, provided that $R_5$ and $R_6$ are not both H;
$R_7$ is selected from H, halo, $C_{1-8}$ alkyl, and phenyl;
$R_8$ and $R_9$ are independently selected from halo, phenyl, $C_{1-9}$ alkyl, $C_{1-8}$ alkoxy, $C_{2-9}$ alkenyl, $C_{2-9}$ alkenyloxy, $C_{3-7}$ cycloalkyl, $C_{3-7}$ cycloalkoxy, $C_{3-7}$cycloalkyl-$C_{1-7}$alkyl, $C_{3-7}$cycloalkyl-$C_{1-7}$alkoxy, $C_{3-7}$cycloalkyloxy-$C_{1-6}$alkyl, and $C_{3-7}$cycloalkyloxy-$C_{1-7}$alkoxy, or $R_8$ and $R_9$ together form $C_{1-9}$ alkylidenyl or $C_{3-9}$ alkenylidenyl; or $R_8$, $R_9$ and the carbon atom to which they are attached together form $C_{3-7}$ cycloalkyl or 5-or 6-membered heterocyclyl;
n is 0, 1 or 2; and
m is 0, 1 or 2;
or a pharmaceutically acceptable salt thereof.
2. The compound of claim 1 wherein X is S or O.
3. The compound of claim 2 wherein X is O.
4. The compound of claim 1 wherein Y is O.
5. The compound of claim 1 wherein Y is S.
6. The compound of claim 1 wherein Z is O.
7. The compound of claim 1 wherein Z is $CH_2$.
8. The compound of claim 1 wherein m is 1.
9. The compound of claim 1 wherein m is 2.
10. The compound of claim 1 wherein n is 1.
11. The compound of claim 1 wherein $R_1$ and $R_2$ are independently selected from H, $C_{1-3}$ alkyl, $C_{1-3}$ alkoxy, F, Cl, and Br.
12. The compound of claim 11 wherein $R_1$ and $R_2$ are independently selected from H, methyl, methoxy, F and Cl.
13. The compound of claim 1 wherein $R_3$ and $R_4$ are independently selected from H, halo, cyano, acetyl, $C_{1-2}$ alkyl, and $C_{1-2}$ alkoxy.
14. The compound of claim 13 wherein $R_3$ is independently selected from H, F, Cl, hydroxy, methyl, and methoxy.
15. The compound of claim 13 wherein $R_4$ is independently selected from F, Cl, methyl, methoxy, trifluoromethyl, trifluoromethoxy, difluoromethyl, difluoromethoxy, fluoromethyl, fluoromethoxy, chlorodifluoromethyl, chlorodifluoromethoxy, dichlorofluoromethyl, and dichlorofluoromethoxy.

16. The compound of claim 1 wherein $R_3$ is selected from methyl, methoxy, H, Cl, Br, I, OH, —$CH(CF_3)_2$, $CF_3$, —$OCF_3$, —$N(CH_3)_2$, —$O$—$CH_2$COOH, and —$COCH_3$, and $R_4$ is selected from H, Cl, and methyl.
17. The compound of claim 1 wherein $R_8$ and $R_9$ together form $C_{1-9}$ alkylidenyl or $C_{3-9}$ alkenylidenyl, or $R_8$, $R_9$ and the carbon atom to which they are attached together form $C_{3-7}$ cycloalkyl.
18. The compound of claim 1 wherein $R_8$ and $R_9$ are independently selected from halo, phenyl, $C_{1-9}$ alkyl, $C_{1-8}$ alkoxy, $C_{2-9}$ alkenyl, $C_{2-9}$ alkenyloxy, $C_{3-7}$ cycloalkyl, $C_{3-7}$ cycloalkoxy, $C_{3-7}$cycloalkyl-$C_{1-7}$alkyl, $C_{3-7}$cycloalkyl-$C_{1-7}$alkoxy, $C_{3-7}$cycloalkyloxy-$C_{1-6}$alkyl, and $C_{3-7}$cycloalkyloxy-$C_{1-7}$alkoxy.
19. The compound of claim 1 wherein $R_3$ is selected from H, F, Cl, methyl, and methoxy, and $R_4$ is selected from F, Cl, acetyl, methyl, methoxy, trifluoromethyl, trifluoromethoxy, difluoromethyl, difluoromethoxy, fluoromethyl, fluoromethoxy, chlorodifluoromethyl, chlorodifluoromethoxy, dichlorofluoromethyl, and dichlorofluoromethoxy.
20. The compound of claim 1 wherein $R_1$ is selected from H, $CF_3$, methyl, Cl, and methoxy, and $R_2$ is selected from H, Cl, and methyl.
21. The compound of claim 1 wherein X is O and Y is O.
22. The compound of claim 1 wherein Z is O and Y is S.
23. The compound of claim 1, wherein X is O and Y is S.
24. The compound of claim 1, wherein X is a covalent bond and Y is S.
25. The compound of claim 1 wherein $R_5$ and $R_6$ are independently $C_{1-4}$ alkyl.
26. The compound of claim 25 wherein $R_5$ and $R_6$ are methyl.
27. The compound of claim 1 wherein
$R_1$ is selected from H, $CF_3$, methyl, Cl, and methoxy;
$R_2$ is selected from H, Cl, and methyl;
$R_3$ is selected from H, F, Cl, methyl, and methoxy; and
$R_4$ is selected from F, Cl, methyl, and methoxy.
28. The compound of claim 1 wherein
X is O;
Y is O;
$R_3$ is selected from H, F, Cl, methyl, and methoxy; and
$R_4$ is selected from F, Cl, methyl, methoxy, trifluoromethyl, trifluoromethoxy, difluoromethyl, difluoromethoxy, fluoromethyl, and fluoromethoxy.
29. The compound of claim 1 wherein
X is O;
Y is S;
$R_3$ is selected from H, F, Cl, methyl, and methoxy; and
$R_4$ is selected from F, Cl, methyl, methoxy, trifluoromethyl, trifluoromethoxy, difluoromethyl, difluoromethoxy, fluoromethyl, and fluoromethoxy.
30. The compound of claim 1 wherein
Y is O;
Z is O;
$R_3$ is selected from H, F, Cl, methyl, and methoxy; and
$R_4$ is selected from F, Cl, methyl, methoxy, methyl, methoxy, trifluoromethyl, trifluoromethoxy, difluoromethyl, difluoromethoxy, fluoromethyl, and fluoromethoxy.
31. The compound of claim 1 wherein
$R_1$ is selected from H, $CF_3$, methyl, Cl, and methoxy;
$R_2$ is selected from H, Cl, and methyl;
$R_3$ is selected from H, F, Cl, methyl, and methoxy;
$R_4$ is selected from F, Cl, methyl, methoxy, and methyl, methoxy, trifluoromethyl, trifluoromethoxy, difluoromethyl, difluoromethoxy, fluoromethyl, and fluoromethoxy; and $R_8$ and $R_9$ together form $C_{1-9}$ alkylidenyl or $C_{3-9}$ alkenylidenyl, or $R_8$, $R_9$ and the carbon atom to which they attach together form $C_{3-7}$ cycloalkyl.

32. The compound of claim 1 wherein
X is O;
Y is O or S; and
Z is O.

33. The compound of claim 1 wherein $R_8$ and $R_9$ together form $C_{1-9}$ alkylidenyl or $C_{3-9}$ alkenylidenyl, or $R_8$, $R_9$ and the carbon atom to which they attach together form $C_{3-7}$ cycloalkyl.

34. The compound of claim 1 wherein $R_8$ and $R_9$ are independently selected from halo, phenyl, $C_{1-9}$ alkyl, $C_{1-8}$ alkoxy, $C_{2-9}$ alkenyl, $C_{2-9}$ alkenyloxy, $C_{3-7}$ cycloalkyl, $C_{3-7}$ cycloalkoxy, $C_{3-7}$cycloalkyl-$C_{1-7}$alkyl, $C_{3-7}$cycloalkyl-$C_{1-7}$alkoxy, $C_{3-7}$cycloalkyloxy-$C_{1-6}$alkyl, and $C_{3-7}$cycloalkyloxy-$C_{1-7}$alkoxy.

35. The compound of claim 34 wherein m is 1 and n is 1.

36. The compound of claim 34 wherein Y is S.

37. The compound of claim 1 wherein $R_5$ and $R_6$ are independently selected from H and $C_{1-8}$ alkyl.

38. The compound of claim 37 wherein $R_5$ and $R_6$ are both methyl, both X and Z are O, $R_7$ is H, and $R_8$ and $R_9$ form $=CH_2$.

39. A pharmaceutical composition comprising a compound of claim 1 and a pharmaceutically acceptable carrier.

40. A method for treating or inhibiting the progression of a PPAR-delta mediated condition selected from the group consisting of diabetes, nephropathy, neuropathy, retinopathy, polycystic ovary syndrome, hypertension, ischemia, stroke, irritable bowel disorder, inflammation, cataract, cardiovascular diseases, Metabolic X Syndrome, hyper-LDL-cholesterolemia, hypertriglyceridemia, hypercholesterolemia, mixed hyperlipidemia, hypo-HDL-cholesterolemia, atherosclerosis, obesity, and complications thereof, said method comprising administering to a patient in need of treatment a pharmaceutically effective amount of the composition of claim 1.

* * * * *

UNITED STATES PATENT AND TRADEMARK OFFICE
CERTIFICATE OF CORRECTION

PATENT NO. : 7,425,649 B2  Page 1 of 1
APPLICATION NO. : 11/226645
DATED : September 16, 2008
INVENTOR(S) : Kuo et al.

It is certified that error appears in the above-identified patent and that said Letters Patent is hereby corrected as shown below:

Column 48

Line 5, delete ", $_{-O-CH_2}$COOH" and insert --, -O-CH$_2$COOH--.

Signed and Sealed this

Sixteenth Day of March, 2010

David J. Kappos
*Director of the United States Patent and Trademark Office*